(12) United States Patent
Mortarino

(10) Patent No.: US 8,746,014 B2
(45) Date of Patent: Jun. 10, 2014

(54) METHOD FOR MAKING A KNITTED MESH

(75) Inventor: Enrico Mortarino, Hickory, NC (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/587,040

(22) Filed: Aug. 16, 2012

(65) Prior Publication Data

US 2012/0304702 A1  Dec. 6, 2012

Related U.S. Application Data

(62) Division of application No. 12/680,404, filed as application No. PCT/US2009/063717 on Nov. 9, 2009.

(60) Provisional application No. 61/122,520, filed on Dec. 15, 2008.

(51) Int. Cl.
*D04B 1/22* (2006.01)

(52) U.S. Cl.
USPC .............................................. 66/170; 66/202

(58) Field of Classification Search
USPC .......... 66/84 R, 203, 87, 88, 169 R, 170, 195, 66/202
See application file for complete search history.

(56) References Cited

U.S. PATENT DOCUMENTS

| | | | |
|---|---|---|---|
| 848,605 A | 3/1907 | Schmid | |
| 1,709,662 A | 4/1929 | Ellis | |
| 1,815,279 A | 7/1931 | Takamine, Jr. | |
| 1,828,736 A | 10/1931 | Harvey | |
| 1,896,494 A | 2/1933 | Myers | |
| 1,921,022 A | 8/1933 | Burton | |
| 1,990,588 A | 2/1935 | Fink | |
| 2,040,949 A | 5/1936 | Olpin | |
| 3,595,276 A | 7/1971 | Wrzesien | |
| 3,931,721 A | 1/1976 | Adamson | |
| 4,089,071 A | 5/1978 | Kainberz | |
| 4,118,842 A | 10/1978 | Norris | |
| 4,141,207 A | 2/1979 | Mizushima | |

(Continued)

FOREIGN PATENT DOCUMENTS

| | | |
|---|---|---|
| DE | 3917174 | 12/1990 |
| DE | 19928635 | 10/2000 |

(Continued)

OTHER PUBLICATIONS

Altman, Gregory et al, Silk-Based Biomaterials, Biomaterials, 2003, 401-416, 24.

(Continued)

*Primary Examiner* — Danny Worrell
(74) *Attorney, Agent, or Firm* — Stephen Donovan

(57) ABSTRACT

A biocompatible surgical silk mesh prosthetic device employs a knit pattern that substantially prevents unraveling and preserves the stability of the mesh device, especially when the mesh device is cut. An example prosthetic device employs a knitted mesh including at least two yarns laid in a knit direction and engaging each other to define a plurality of nodes. The at least two yarns include a first yarn and a second yarn extending between and forming loops about two nodes. The second yarn has a higher tension at the two nodes than the first yarn. the second yarn substantially prevents the first yarn from moving at the two nodes and substantially prevents the knitted mesh from unraveling at the nodes.

6 Claims, 27 Drawing Sheets

(56) References Cited

U.S. PATENT DOCUMENTS

| | | |
|---|---|---|
| 4,340,091 A | 7/1982 | Skelton |
| 4,792,336 A | 12/1988 | Hlawacek |
| 4,816,028 A | 3/1989 | Kapadia |
| 4,942,875 A | 7/1990 | Hlawacek |
| 4,984,570 A | 1/1991 | Langen |
| 5,120,829 A | 6/1992 | Pierschbacher |
| 5,134,006 A | 7/1992 | Irvin |
| 5,171,505 A | 12/1992 | Lock |
| 5,178,630 A | 1/1993 | Schmitt |
| 5,250,077 A | 10/1993 | Fuse |
| 5,252,285 A | 10/1993 | Lock |
| 5,366,504 A | 11/1994 | Andersen |
| 5,385,836 A | 1/1995 | Kimura |
| 5,456,697 A | 10/1995 | Chesterfield |
| 5,456,711 A * | 10/1995 | Hudson ............................ 623/1.5 |
| 5,509,931 A | 4/1996 | Schmitt |
| 5,569,273 A | 10/1996 | Titone et al. |
| 5,587,456 A | 12/1996 | Pierschbacher |
| 5,591,822 A | 1/1997 | Pierschbacher |
| 5,598,615 A | 2/1997 | Takada |
| 5,606,019 A | 2/1997 | Cappello |
| 5,674,276 A | 10/1997 | Andersen |
| 5,760,176 A | 6/1998 | Pierschbacher |
| 5,771,716 A | 6/1998 | Schlussel |
| 5,849,040 A | 12/1998 | Kanehisa |
| 5,919,232 A | 7/1999 | Chaffringeon |
| 5,951,506 A | 9/1999 | Tsubouchi |
| 5,990,378 A | 11/1999 | Ellis |
| 6,042,592 A | 3/2000 | Schmitt |
| 6,090,116 A | 7/2000 | D'Aversa et al. |
| 6,110,590 A | 8/2000 | Zarkoob |
| 6,113,623 A | 9/2000 | Sgro |
| 6,136,022 A | 10/2000 | Nunez |
| 6,146,418 A | 11/2000 | Berman |
| 6,164,339 A | 12/2000 | Greenhalgh |
| 6,175,533 B1 | 1/2001 | Lee |
| 6,228,132 B1 | 5/2001 | Prince |
| 6,287,316 B1 | 9/2001 | Agarwal |
| 6,287,340 B1 | 9/2001 | Altman |
| 6,302,922 B1 | 10/2001 | Kanehisa |
| 6,303,136 B1 | 10/2001 | Li |
| 6,408,656 B1 | 6/2002 | Ory et al. |
| 6,440,740 B1 | 8/2002 | Tsubouchi |
| 6,443,964 B1 | 9/2002 | Ory et al. |
| 6,540,773 B2 | 4/2003 | Dong |
| 6,592,617 B2 | 7/2003 | Thompson |
| 6,638,284 B1 | 10/2003 | Rousseau |
| 6,729,356 B1 | 5/2004 | Baker |
| 6,737,371 B1 | 5/2004 | Planck et al. |
| 6,773,459 B2 | 8/2004 | Dauner |
| 6,783,554 B2 | 8/2004 | Amara et al. |
| 6,827,743 B2 | 12/2004 | Eisermann |
| 6,848,281 B2 | 2/2005 | Ishihara et al. |
| 6,866,681 B2 | 3/2005 | Laboureau |
| 6,902,932 B2 | 6/2005 | Altman |
| 6,946,003 B1 | 9/2005 | Wolowacz |
| 6,966,918 B1 | 11/2005 | Schuldt-Hempe |
| 6,971,252 B2 | 12/2005 | Therin |
| 7,021,086 B2 | 4/2006 | Ory et al. |
| 7,025,063 B2 | 4/2006 | Snitkin |
| 7,115,388 B2 | 10/2006 | Tsubouchi |
| 7,156,858 B2 | 1/2007 | Schuldt-Hempe |
| 7,166,570 B2 | 1/2007 | Hunter |
| 7,285,637 B2 | 10/2007 | Armato |
| 7,293,433 B1 | 11/2007 | McMurray |
| 7,338,531 B2 | 3/2008 | Ellis |
| 7,341,601 B2 | 3/2008 | Eisermann |
| 7,476,249 B2 | 1/2009 | Frank |
| 7,614,258 B2 | 11/2009 | Cherok |
| 7,824,701 B2 | 11/2010 | Binette |
| 7,828,855 B2 | 11/2010 | Ellis |
| 7,842,780 B2 | 11/2010 | Kaplan |
| 7,875,074 B2 | 1/2011 | Chen |
| 7,900,484 B2 | 3/2011 | Cherok et al. |
| 8,007,531 B2 | 8/2011 | Frank |
| 8,177,834 B2 | 5/2012 | Carlson |
| 8,197,542 B2 | 6/2012 | Becker |
| 8,202,317 B2 | 6/2012 | Becker |
| 8,226,715 B2 | 7/2012 | Hwang |
| 8,418,508 B2 * | 4/2013 | Lecuivre et al. ................. 66/195 |
| 2002/0156437 A1 | 10/2002 | McDevitt |
| 2003/0087433 A1 | 5/2003 | Tsubouchi |
| 2003/0106346 A1 | 6/2003 | Matsumoto |
| 2003/0165548 A1 | 9/2003 | Tsubouchi |
| 2003/0183978 A1 | 10/2003 | Asakura |
| 2004/0005363 A1 | 1/2004 | Tsukada |
| 2004/0029478 A1 * | 2/2004 | Planck et al. .................. 442/318 |
| 2004/0170827 A1 | 9/2004 | Crighton |
| 2004/0176658 A1 * | 9/2004 | McMurray ...................... 600/37 |
| 2004/0219630 A1 | 11/2004 | Tsubouchi |
| 2004/0224406 A1 | 11/2004 | Altman |
| 2005/0089552 A1 | 4/2005 | Altman |
| 2005/0228408 A1 * | 10/2005 | Fricke et al. .................. 606/151 |
| 2005/0240261 A1 | 10/2005 | Rakos |
| 2005/0260706 A1 | 11/2005 | Kaplan |
| 2005/0288797 A1 | 12/2005 | Howland |
| 2006/0009835 A1 | 1/2006 | Osborne |
| 2006/0013950 A1 | 1/2006 | Porter |
| 2007/0088434 A1 | 4/2007 | Frank |
| 2007/0207186 A1 | 9/2007 | Scanlon |
| 2008/0038236 A1 | 2/2008 | Gimble |
| 2008/0131509 A1 | 6/2008 | Hossainy |
| 2008/0176960 A1 | 7/2008 | Tsukada |
| 2008/0200086 A1 | 8/2008 | Porter |
| 2008/0206302 A1 | 8/2008 | Sittinger et al. |
| 2008/0228028 A1 | 9/2008 | Carlson |
| 2008/0300683 A1 | 12/2008 | Altman |
| 2009/0024162 A1 | 1/2009 | Shalaby |
| 2009/0030454 A1 | 1/2009 | Knight |
| 2009/0214649 A1 | 8/2009 | Gazit |
| 2010/0023029 A1 | 1/2010 | Young |
| 2010/0145367 A1 | 6/2010 | Ratcliffe |
| 2010/0209405 A1 | 8/2010 | Altman |
| 2010/0249924 A1 | 9/2010 | Powell |
| 2010/0256756 A1 | 10/2010 | Altman |
| 2011/0009960 A1 | 1/2011 | Altman |
| 2011/0022171 A1 | 1/2011 | Richter |
| 2011/0054604 A1 | 3/2011 | Becker |
| 2011/0054605 A1 | 3/2011 | Becker |
| 2011/0106249 A1 | 5/2011 | Becker |
| 2011/0167602 A1 | 7/2011 | Altman |
| 2011/0171453 A1 | 7/2011 | Altman |
| 2011/0184227 A1 | 7/2011 | Altman |
| 2011/0189773 A1 | 8/2011 | Altman |
| 2011/0190795 A1 | 8/2011 | Hotter et al. |
| 2011/0224703 A1 | 9/2011 | Mortarino |
| 2011/0257665 A1 | 10/2011 | Mortarino |
| 2011/0257761 A1 | 10/2011 | Mortarino |
| 2011/0282365 A1 | 11/2011 | Hadba et al. |
| 2011/0301717 A1 | 12/2011 | Becker |
| 2012/0053690 A1 | 3/2012 | Frank |
| 2012/0165957 A1 | 6/2012 | Everland et al. |
| 2012/0184974 A1 | 7/2012 | Becker |
| 2012/0226352 A1 | 9/2012 | Becker |
| 2012/0244143 A1 | 9/2012 | Lo et al. |

FOREIGN PATENT DOCUMENTS

| | | |
|---|---|---|
| EP | 0677297 | 10/1995 |
| EP | 1241178 | 9/2002 |
| EP | 0889156 | 8/2003 |
| EP | 2016956 | 1/2009 |
| EP | 2068766 | 10/2011 |
| EP | 2068766 B1 | 10/2011 |
| JP | 06-245989 | 9/1994 |
| WO | 95-25550 | 9/1995 |
| WO | 00-57812 | 10/2000 |
| WO | 00-72782 | 12/2000 |
| WO | 02-29141 | 4/2002 |
| WO | 2004-062697 | 7/2004 |
| WO | 2005-123114 | 12/2005 |
| WO | 2006102477 | 9/2006 |
| WO | 2006102477 A2 | 9/2006 |

(56) References Cited

FOREIGN PATENT DOCUMENTS

| | | |
|---|---|---|
| WO | 2009-023615 | 2/2009 |
| WO | 2010-074827 | 7/2010 |
| WO | 2010-141133 | 12/2010 |

OTHER PUBLICATIONS

Cappello, J. et al, In-Situ Self-Assembling Protein Polymer Gel Systems for Administration, Delivery, and Release of Drugs, Journal of Controlled Release, 1998, 105-117, 53.

Horan, R.L. et al, Biological and Biomechanical Assessment of a Long-Term Bioresorbable Silk-Derived Surgical Mesh in an Abdominal Body Wall Defect Model, Hernia, 2009, 189-199, 13.

Horan, Rebecca et al, In Vitro Degradation of Silk Fibroin, Biomaterials, 2005, 3385-3393, 26.

Kardestuncer, T. et al, RGD-Tethered Silk Substrate Stimulates the Differentiation of Human Tendon Cells, Clinical Orthopaedics and Related Research, 2006, 234-239, 448.

Kundu, Subhas et al, Natural Protective Glue Protein, Sericin Bioengineered by Silkworms: Potential for Biomedical and Biotechnological Applications, Progess in Polymer Science, 2008, 998-1012, 33.

Panilaitis, Bruce et al, Macrophage Responses to Silk, Biomaterials, 2003, 3079-3085, 24.

Tamada, Yasushi et al, Cell Adhesion and Growth on Various Kinds of Silk Fabrics, Sen-i Gakkai Symp. Preprints, 1998, 1-4.

Tsukada, Masuhiro et al, Preparation and Application of Porous Silk Fibroin Materials, Journal of Applied Polymer Science, 1994, 507-514, 54.

Yanagisawa, Satoshi et al, Improving Cell-Adhesive Properties of Recombinant Bombyx Mori Silk by Incorporation of Collagen or Fibronectin Derived Peptides Produced by Transgenic Silkworms, Biomacromolecules, 2007, 3487-3492, 8.

Zhu, Zhenghua et al, Preparation and Characterization of Regenerated Bombyx Mori Silk Fibroin Fiber Containing Recombinant Cell-Adhesive Proteins; Nonowoven Fiber and Monofilament, J. Appl. Polym. Sci., 2008, 2956-2963, 109.

\* cited by examiner

METHOD FOR MAKING A KNITTED MESH

CROSS-REFERENCE TO RELATED APPLICATIONS

This application is a divisional of U.S. patent application Ser. No. 12/680,404, filed Sep. 19, 2011, which is a national stage application under 35 USC §371 of PCT Patent Application No. PCT/US2009/063717, filed Nov. 9, 2009, which claims priority to U.S. Provisional Patent Application No. 61/122,520, filed Dec. 15, 2008, the contents of each of which are incorporated entirely herein by reference.

BACKGROUND OF THE INVENTION

1. Field of the Invention

The present invention generally relates to a prosthetic device for tissue repair, and, more particularly, to a surgical silk mesh device employing a stable knit structure.

2. Description of Related Art

Surgical mesh initially used for hernia and abdominal wall defects are now being used for other types of tissue repair, such as rotator cuff repair, pelvic floor dysfunction, and reconstructive or cosmetic surgeries. It is projected that in 2010, there will be more than 8 million hernia procedures, 800,000 rotator cuff repairs, 3 million pelvic prolapse repairs, 600,000 urinary incontinence repairs, and 1.5 million reconstructive or aesthetic plastic surgeries. Most of these procedures will likely employ implantable surgical mesh devices currently on the market, including: Bard Mesh (polypropylene) by C. R. Bard; Dexon (polyglycolic acid) by Synecture/US Surgical; Gore-Tex (polytetrafluoroethylene) by W.L. Gore; Prolene (polypropylene), Prolene Soft (polypropylene), Mersilene Mesh (polyester), Gynemesh (polypropylene), Vicryl Knitted Mesh (polyglactin 910), TVT (polypropylene) by Ethicon; Sparc tape (polypropylene) by American Medical Systems; and IVS tape (polypropylene) by TYCO Healthcare International.

Surgical mesh devices are typically biocompatible and may be formed from bioresorbable materials and/or non-bioresorbable materials. For example, polypropylene, polyester, and polytetrafluoroethylene (PTFE) are biocompatible and non-bioresorbable, while polyglactin 910 and polyglycolic acid are biocompatible and bioresorbable.

Though current surgical mesh devices may be formed from different materials, they have various similar physical and mechanical characteristics beneficial for tissue repair. However, despite the benefits provided by current surgical mesh devices, their use may be accompanied by a variety of complications. Such complications, for example, may include scar encapsulation and tissue erosion, persistent infection, pain, and difficulties associated with revision surgery. In addition, the use of an absorbable material may result in reoccurrence due to rapid resorption of the implant material and loss of strength.

Although polypropylene monofilament may be a highly regarded material for surgical mesh devices, polypropylene mesh devices can induce intense scar formations and create a chronic foreign body reaction with the formation of a fibrous capsule, even years after implantation. Minor complaints of seromas, discomfort, and decreased wall mobility are frequent and observed in about half of the patients implanted with polypropylene mesh devices. Moreover, polypropylene generally cannot be placed next to the bowel due to the propensity of adhesion formation.

Although the use of multifilament polyester may improve conformity with the abdominal wall, it is also associated with a variety of disadvantages. For example, higher incidences of infection, enterocutaneous fistula formation, and small bowel obstruction have been reported with the use of multifilament polyester compared to other materials. Indeed, the small interstices of the multifilament yarn make it more susceptible to the occurrence of infection, and thus multifilament polyester is not commonly used within the United States.

The use of polytetrafluoroethylene (PTFE) may be advantageous in minimizing adhesions to the bowel. However, the host tissue encapsulates the PTFE mesh, resulting in weak in-growth in the abdominal wall and weaker hernia repair. This material, though not a good mesh material on its own, has found its place as an adhesion barrier.

Absorbable materials, such as Vicryl and Dexon, used for hernia repair have the advantage of being placed in direct contact with the bowel without adhesion or fistula formation. A study has observed that Vicryl has comparable burst strength to nonabsorbable mesh at three weeks but is significantly weaker at twelve weeks due to a quick absorption rate. Meanwhile, the same study observed that Dexon has more in-growth at twelve weeks with less absorption of the mesh. The concern with absorbable meshes is that the rate of absorption is variable, possibly leading to hernia recurrence if the proper amount of new tissue is not there to withstand the physiologic stresses placed on the hernia defect.

A significant characteristic of a biomaterial is its porosity, because porosity is the main determinant for tissue reaction. Pore sizes of >500-600 µm permit in-growth of soft tissue; pore sizes of >200-300 µm favor neo-vascularisation and allow mono-morphological restitution of bony defects; pore sizes of <200 µm are considered to be almost watertight, hindering liquid circulation at physiological pressures; and pores of <100 µm only lead to in-growth of single cell types instead of building new tissues. Finally, a pore size of <10 µm hinders any in-growth and increases the chance of infection, sinus tract formation, and encapsulation of the mesh. Bacteria averaging 1 µm in size can hide in the small interstices of the mesh and proliferate while protected from neutrophilic granulocytes averaging 10-15 µm.

Other important physical characteristics for surgical mesh devices include thickness, burst strength, and material stiffness. The thickness of surgical mesh devices vary according to the particular repair procedure. For example, current surgical mesh device hernia, pelvic floor dysfunction, and reconstructive/cosmetic procedures range in thickness from approximately 0.635 mm to 1.1 mm. For rotator cuff repair, a thickness of 0.4 mm to 5 mm is typically employed.

Intra-abdominal pressures of 10-16 N, with a mean distension of 11-32% results in the need for a surgical mesh with a burst strength that can resist the stress of the inner abdomen before healthy tissue comes into being.

Material stiffness is an important mechanical characteristic for surgical mesh, especially when used for pelvic floor dysfunction, because material stiffness has been associated with the likelihood of tissue erosion. Surgical mesh devices formed from TVT, IVS, Mersilene, Prolene, Gynemesh, Sparc tape, for example, currently have an ultimate tensile strength (UTS) that exceeds the forces exerted by intra-abdominal pressures of 10-16 N. With the low force in the abdomen, the initial stiffness of the material is an important consideration. Moreover, the stiffness may exhibit non-linear behavior most likely due to changes in the fabric structure, e.g., unraveling of the knit, weave, etc. A surgical mesh device of lesser stiffness may help reduce tissue erosion and may conform to the contours of the body more effectively.

SUMMARY OF THE INVENTION

In view of the disadvantages of current surgical mesh devices, there continues to be a need for a surgical mesh that is biocompatible and absorbable, has the ability to withstand the physiological stresses placed on the host collagen, and minimizes tissue erosion, fistulas, or adhesions. Thus, embodiments according to aspects of the present invention provide a biocompatible surgical silk mesh prosthetic device for use in soft and hard tissue repair. Examples of soft tissue repair include hernia repair, rotator cuff repair, cosmetic surgery, implementation of a bladder sling, or the like. Examples of hard tissue repair, such as bone repair, involve reconstructive plastic surgery, ortho trauma, or the like.

Advantageously, the open structure of these embodiments allows tissue in-growth while the mesh device degrades at a rate which allows for a smooth transfer of mechanical properties to the new tissue from the silk scaffold. According to a particular aspect of the present invention, embodiments employ a knit pattern, referred to as a "node-lock" design. The "node-lock" design substantially prevents unraveling and preserves the stability of the mesh device, especially when the mesh device is cut.

In a particular embodiment, a prosthetic device includes a knitted mesh including at least two yarns laid in a knit direction and engaging each other to define a plurality of nodes, the at least two yarns including a first yarn and a second yarn extending between and forming loops about two nodes, the second yarn having a higher tension at the two nodes than the first yarn, the second yarn substantially preventing the first yarn from moving at the two nodes and substantially preventing the knitted mesh from unraveling at the nodes.

In an example of this embodiment, the first yarn and the second yarn are formed from different materials. In another example of this embodiment, the first yarn and the second yarn have different diameters. In further embodiments, wherein the first yarn and the second yarn have different elastic properties. In yet a further example of this embodiment, the at least two yarns are formed from silk.

In another example of this embodiment, a first length of the first yarn extends between the two nodes and a second length of the second yarn extends between the two nodes, the first length being greater than the second length. For instance, the first yarn forms an intermediate loop between the two nodes and the second yarn does not form a corresponding intermediate loop between the two nodes. The first length of the first yarn is greater than the second length of the second yarn.

In yet another example of this embodiment, the first yarn is included in a first set of yarns and the second yarn is included in a second set of yarns, the first set of yarns being applied in a first wale direction, each of the first set of yarns forming a first series of loops at each of a plurality of courses for the knitted mesh, the second set of yarns being applied in a second wale direction, the second wale direction being opposite from the first wale direction, each of the second set of yarns forming a second series of loops at every other of the plurality of courses for the knitted mesh, the first set of yarns interlacing with the second set of yarns at the every other course to define the nodes for the knitted mesh, the second set of yarns having a greater tension than the first set of yarns, the difference in tension substantially preventing the knitted mesh from unraveling at the nodes.

In a further example of this embodiment, the first yarn is included in a first set of yarns and the second yarn is included in a second set of yarns, the first set of yarns and the second set of yarns being alternately applied in a wale direction to form staggered loops, the first set of yarns interlacing with the second set of yarns to define the nodes for the knitted mesh, the alternating application of the first set of yarns and the second set of yarns causing the first set of yarns to have different tensions relative to the second set of yarns at the nodes, the difference in tension substantially preventing the knitted mesh from unraveling at the nodes.

In yet a further example of this embodiment, the first yarn is included in a first set of yarns and the second yarn is included in a second set of yarns, the first set of yarns forming a series of jersey loops along each of a first set of courses for a knitted mesh, the second set of yarns forming a second series of alternating tucked loops and jersey loops along each of a second set of courses for the knitted mesh, the second set of courses alternating with the first set of courses, the second set of yarns having a greater tension than the first set of yarns, the tucked loops of the second set of yarns engaging the jersey loops of the first set of yarns to define nodes for the knitted mesh, the tucked loops substantially preventing the knitted mesh from unraveling at the nodes.

In another particular embodiment, a method for making a knitted mesh for a prosthetic device, includes: applying a first set of yarns in a first wale direction on a single needle bed machine, each of the first set of yarns forming a first series of loops at each of a plurality of courses for a knitted mesh; applying a second set of yarns in a second wale direction on the single needle bed machine, the second wale direction being opposite from the first wale direction, each of the second set of yarns forming a second series of loops at every other of the plurality of courses for the knitted mesh; and applying a third set of yarns in every predetermined number of courses for the knitted mesh, the application of the third set of yarns defining openings in the knitted mesh, wherein the first set of yarns interlaces with the second set of yarns at the every other course to define nodes for the knitted mesh, and the second set of yarns has a greater tension than the first set of yarns, the difference in tension substantially preventing the knitted mesh from unraveling at the nodes.

In yet another embodiment, a method for making a knitted mesh for a prosthetic device, includes: applying a first set of yarns to a first needle bed of a double needle bed machine in a wale direction; applying a second set of yarns to a second needle bed of the double needle bed machine in a wale direction; and applying a third set of yarns in every predetermined number of courses for the knitted mesh, the application of the third set of yarns defining openings in the knitted mesh, wherein the first set of yarns and the second set of yarns are alternately applied to form staggered loops at the first needle bed and the second needle bed, respectively, and the first set of yarns interlaces with the second set of yarns to define nodes for the knitted mesh, the alternating application of the first set of yarns and the second set of yarns causing the first set of yarns to have a different tension relative to the second set of yarns at the nodes, the difference in tension substantially preventing the knitted mesh from unraveling at the nodes.

In a further particular embodiment, a method for making a knitted mesh for a prosthetic device, includes: forming, on a flat needle bed machine, a first series of jersey loops along each of a first set of courses for a knitted mesh; and forming, on the flat needle bed machine, a second series of alternating tucked loops and jersey loops along each of a second set of courses for the knitted mesh, the second set of courses alternating with the first set of courses; wherein the second set of courses has a greater tension than the first set of courses, and the tucked loops along the second set of courses engage the jersey loops of the first set of courses and substantially prevents the knitted mesh from unraveling at the tucked loops. In an example of this embodiment, a continuous yarn forms the first set of courses and the second set of courses. In another example of this embodiment, the first set of courses and the second set of courses are formed by different yarns. In yet another example of this embodiment, the first set of courses and the second set of courses are formed by different yarns having different diameters.

These and other aspects of the present invention will become more apparent from the following detailed description of the preferred embodiments of the present invention when viewed in conjunction with the accompanying drawings.

DETAILED DESCRIPTION

Figure 1B:
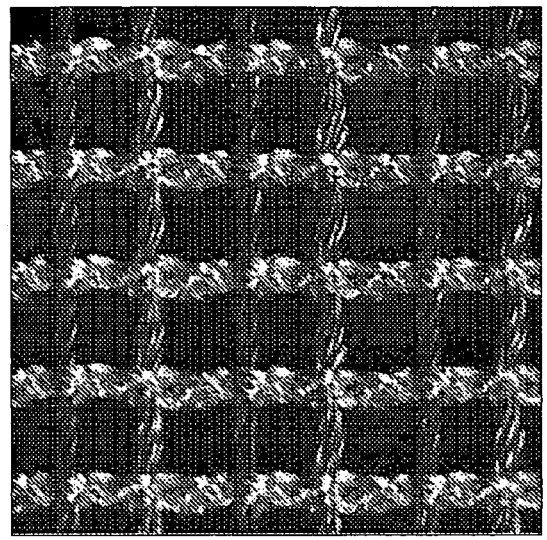
FIG. 1B illustrates the technical front of the example mesh illustrated in FIG. 1A.

Embodiments according to aspects of the present invention provide a biocompatible surgical silk mesh device for use in soft or hard tissue repair. Examples of soft tissue repair include hernia repair, rotator cuff repair, cosmetic surgery, implementation of a bladder sling, or the like. Examples of hard tissue repair, such as bone repair, involve reconstructive plastic surgery, ortho trauma, or the like.

Advantageously, the open structure of these embodiments allows tissue in-growth while the mesh bioresorbs at a rate which allows for a smooth transfer of mechanical properties to the new tissue from the silk scaffold. Furthermore, embodiments employ a knit pattern that substantially prevents unraveling, especially when the mesh device is cut. In particular, embodiments may preserve the stability of the mesh device by employing a knit pattern that takes advantage of variations in tension between at least two yarns laid in a knit direction. For example, a first yarn and a second yarn may be laid in a knit direction to form "nodes" for a mesh device. The knit direction for the at least two yarns, for example, may be vertical during warp knitting or horizontal during weft knitting. The nodes of a mesh device, also known as intermesh loops, refer to intersections in the mesh device where the two yarns form a loop around a knitting needle. In some embodiments, the first yarn is applied to include greater slack than the second yarn, so that, when a load is applied to the mesh device, the first yarn is under a lower tension than the second device. A load that places the at least two yarns under tension may result, for example, when the mesh device is sutured or if there is pulling on the mesh device. The slack in the first yarn causes the first yarn to be effectively larger in diameter than the second yarn, so that the first yarn experiences greater frictional contact with the second yarn at a node and cannot move, or is "locked," relative to the second yarn. Accordingly, this particular knit design may be referred to as a "node-lock" design.

In general, node-lock designs according to aspects of the present invention employ at least two yarns under different tensions, where a higher tension yarn restricts a lower tension yarn at the mesh nodes. To achieve variations in tension between yarns, other node-lock designs may vary the yarn diameter, the yarn materials, the yarn elastic properties, and/or the knit pattern. For example, the knit pattern described previously applies yarns in varying lengths to create slack in some yarns so that they experience less tension. Because the lower tension yarn is restricted by the higher tension yarn, node-lock designs substantially prevent unraveling of the mesh when the mesh is cut. As such, the embodiments allow the mesh device to be cut to any shape or size while maintaining the stability of the mesh device. In addition, node-lock designs provide a stability that makes it easy to pass the mesh device through a cannula for laparoscopic or arthroscopic surgeries without damaging the material.

Although the node-lock design may employ a variety of polymer materials, a mesh device using silk according to aspects of the present invention can bioresorb at a rate sufficient to allow tissue in-growth while slowly transferring the load-bearing responsibility to the native tissue. Particular embodiments may be formed from *Bombyx mori* silkworm silk fibroin. The raw silk fibers have a natural globular protein coating known as sericin, which may have antigenic properties and must be depleted before implantation. Accordingly, the yarn is taken through a depletion process. The depletion of sericin is further described, for example, by Gregory H. Altman et al., "Silk matrix for tissue engineered anterior cruciate ligaments," Biomaterials 23 (2002), pp. 4131-4141, the contents of which are incorporated herein by reference. As a result, the silk material used in the device embodiments contains substantially no sensitizing agents, in so far as can be measured or predicted with standardized biomaterials test methods.

Figure 22:
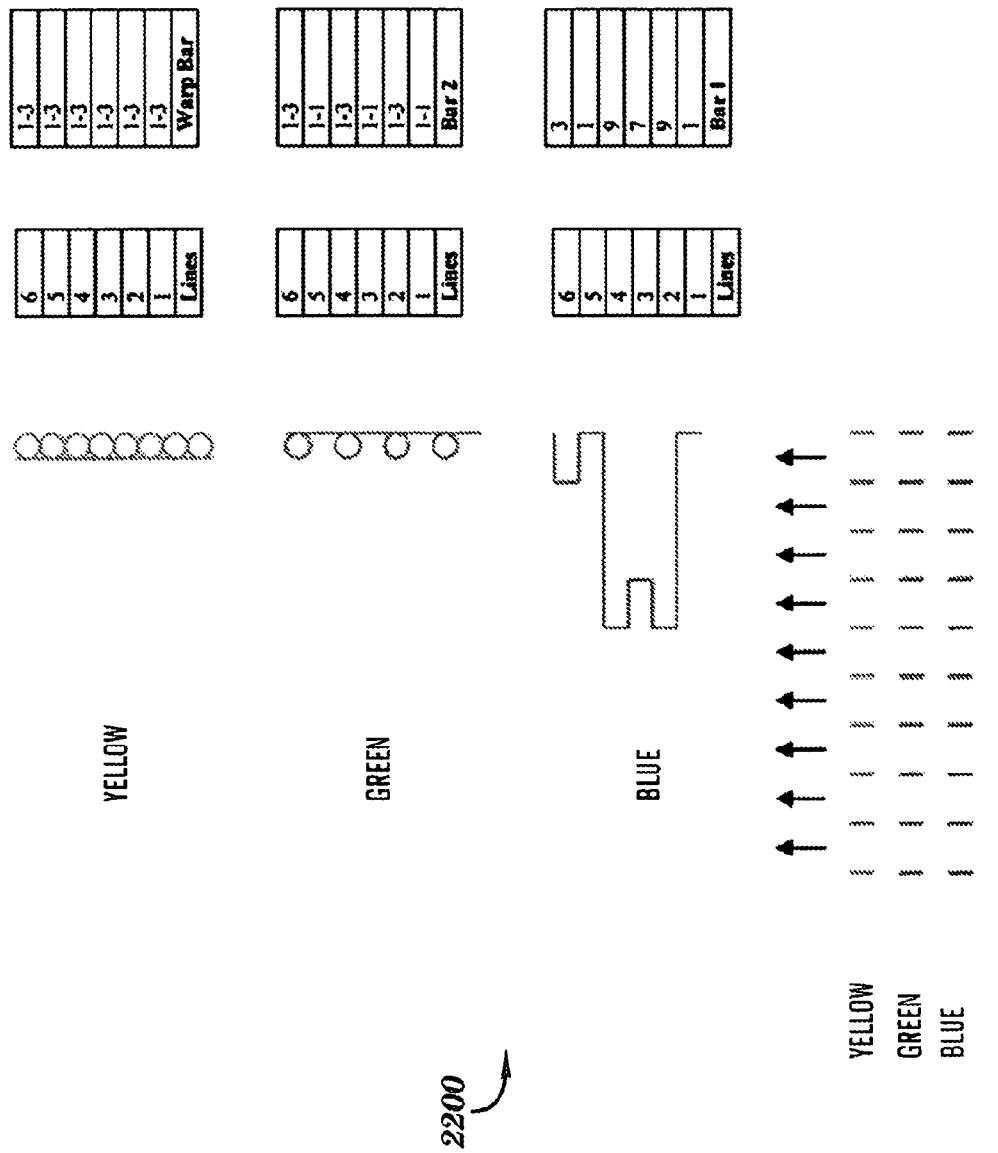
FIG. 22 illustrates an example pattern layout for a single needle bed mesh according to aspects of the present invention.

A surgical mesh device according to aspects of the present invention may be created on a single needle bed Comez Acotronic/600-F or a Comez 410 ACO by the use of three movements as shown in the pattern layout 2200 in FIG. 22: two movements in the wale direction, the vertical direction within the fabric, and one in the course direction, the horizontal direction of the fabric. The movements in the wale direction go in opposing directions; a first yarn moving in one direction loops every course while the second yarn moving in the opposite direction loops every other course. The yarns follow a repeated pattern of 3-1 and 1-1/1-3 on a 20 gauge knitting machine, using only half of the needles available on the needle bed. The interlacing of the loops within the fabric allow for one yarn to become under more tension than the other under stress, locking it around the less tensioned yarn; keeping the fabric from unraveling when cut. The other movement within the fabric occurs in every few courses creating the openings in the mesh. These yarns follow a pattern of 1-9/9-7/7-9/9-1/1-3/3-1. These yarns create tension within the fabric when under stress, locking the yarns in the fabric; preventing the fabric from unraveling.

Figure 26:
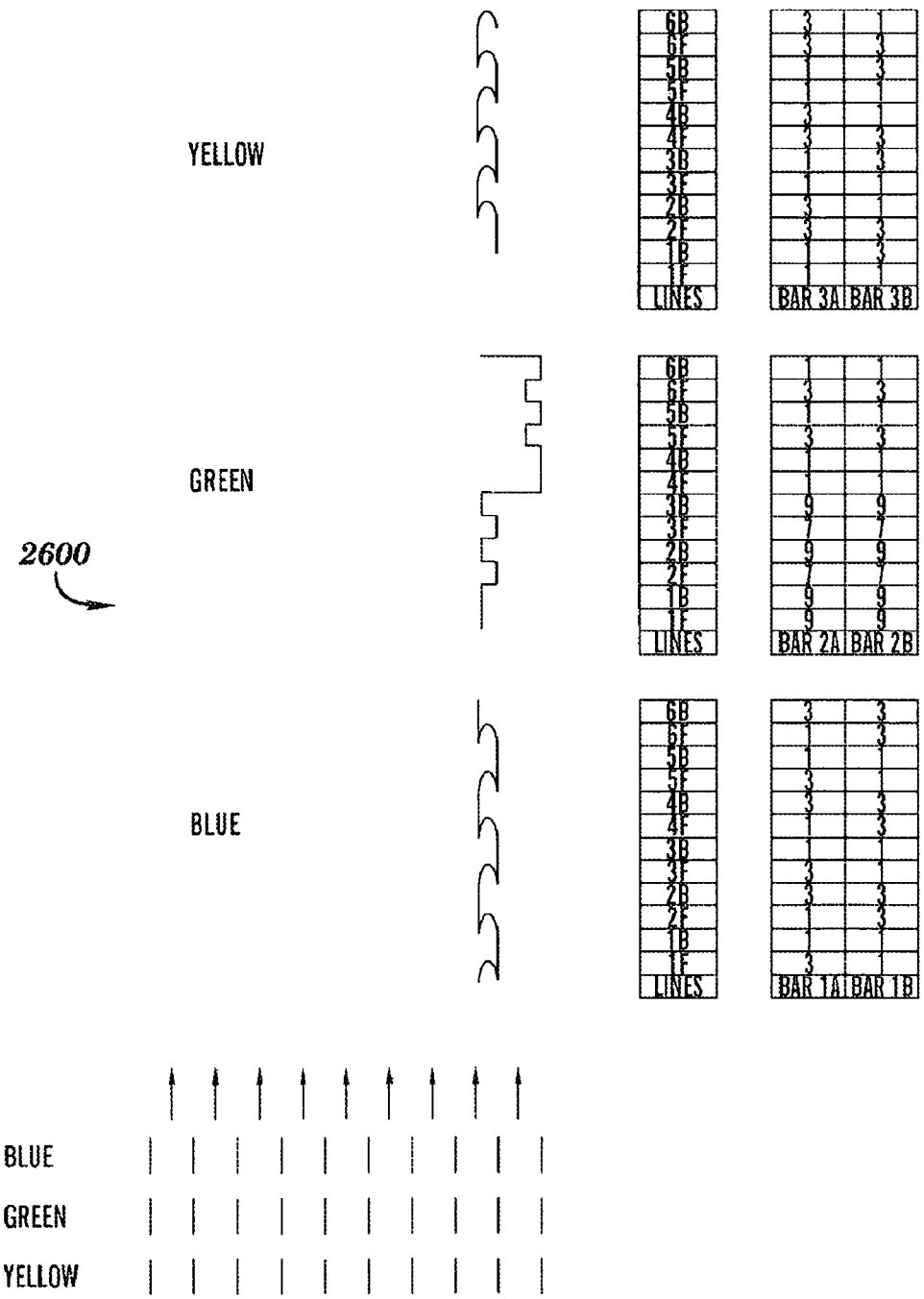
FIG. 26 illustrates an example pattern layout of the double needle bed mesh according to aspects of the present invention.

A surgical mesh device according to aspects of the present invention may be created on a double needle bed Comez DNB/EL-800-8B knitting machine by the use of three movements as shown in the pattern layout 2600 in FIG. 26: two movements in the wale direction and one in the course direction. The two movements in the wale direction occur on separate needle beds with alternate yarns; loops that occur in every course movement are staggered within the repeat. The yarns follow a repeated pattern of 3-1/1-1/1-3/3-3 and 1-1/1-3/3-3/3-1. The third movement happens with the yarn that traverses the width of the fabric. The yarn follows the pattern 9-9/9-9/7-7/9-9/7-7/9-9/1-1/1-1/3-3/1-1/3-3/1-1. This fabric is also made at half gauge on a 20 gauge knitting machine and prevents unraveling due to the tension created between the yarns when stressed. The repeat the yarn follows within the pattern is illustrated in FIG. 26.

Figure 23:
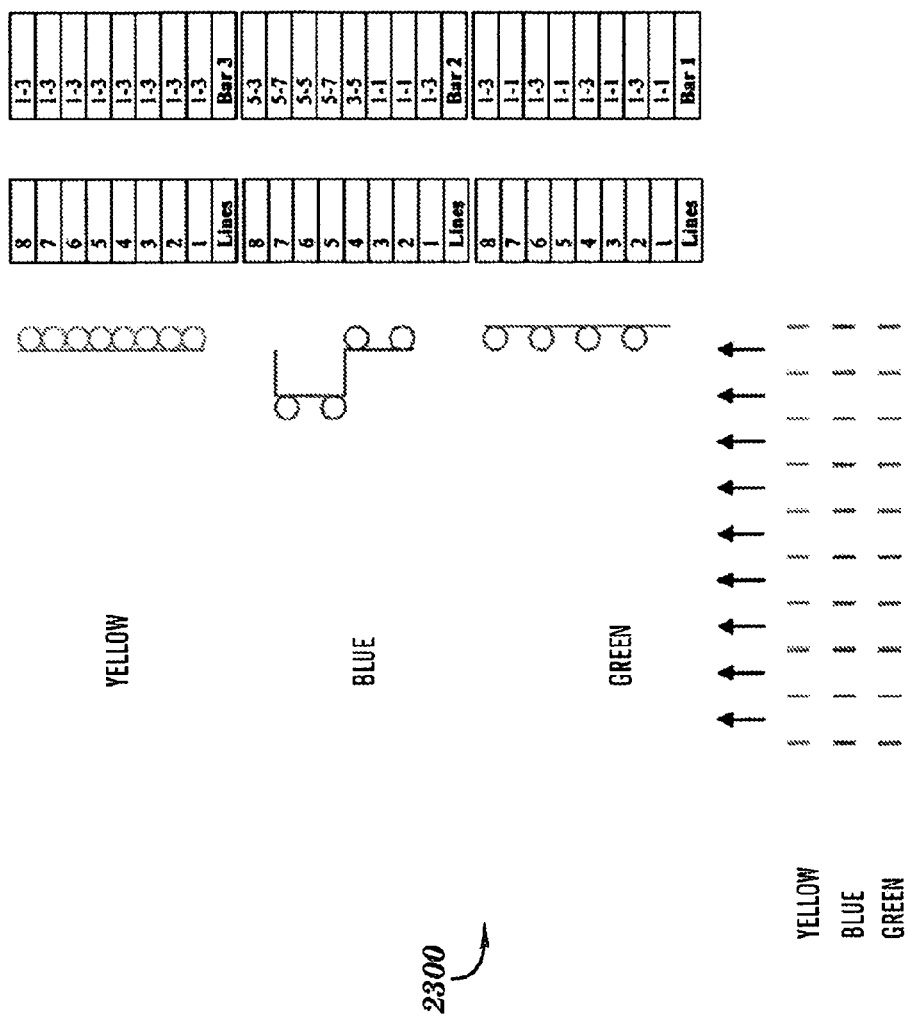
FIG. 23 illustrates an example pattern layout for a single needle bed mesh according to aspects of the present invention.
Figure 24:
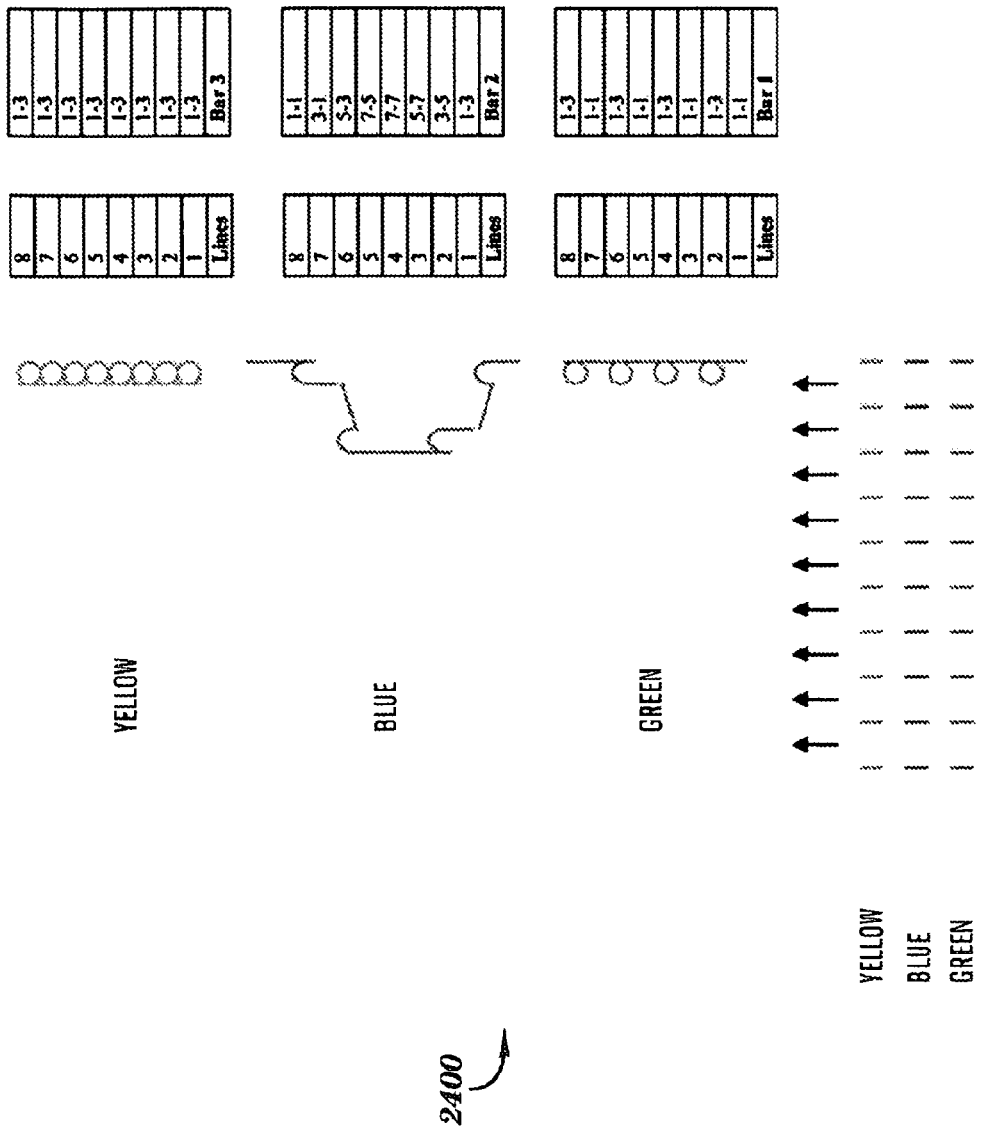
FIG. 24 illustrates an example pattern layout for a single needle bed mesh according to aspects of the present invention.
Figure 25:
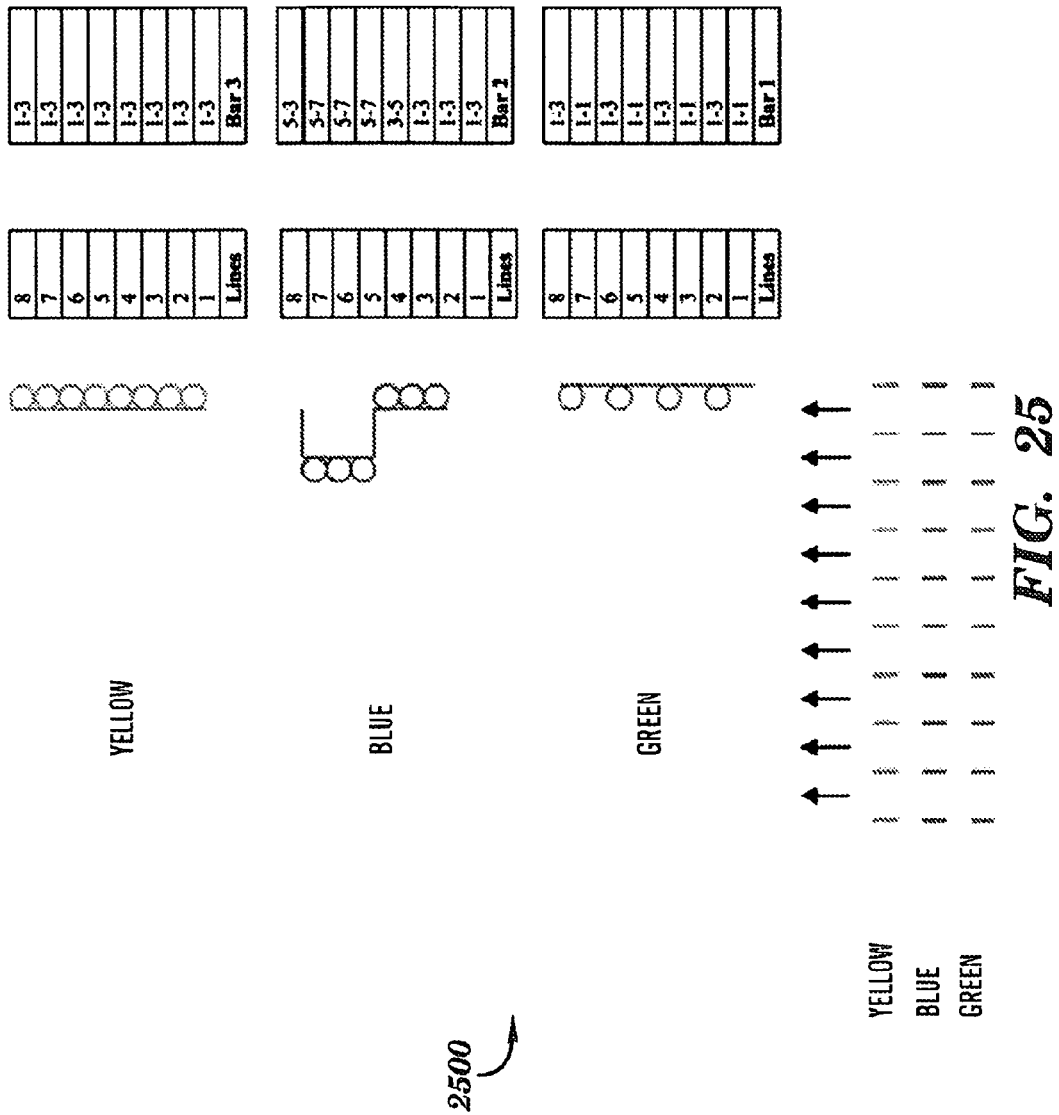
FIG. 25 illustrates an example pattern layout for the single needle bed mesh according to aspects of the present invention.

According to the pattern layouts 2300, 2400, and 2500 illustrated in FIGS. 23, 24 and 25, respectively, variations of the surgical mesh pattern are demonstrated for the Single Needle Bed including knitting with an added warp bar in place of using a weft bar insertion. These variations include knitting with the node lock yarns while moving it perpendicularly to one or more wales. These variations may include, but are not limited to, knitting either an open or closed chain stitch in either all or alternating courses. Utilizing a third warp bar, as opposed to a weft bar insertion can also be applied to the double needle warp knitting machine.

Figure 27:
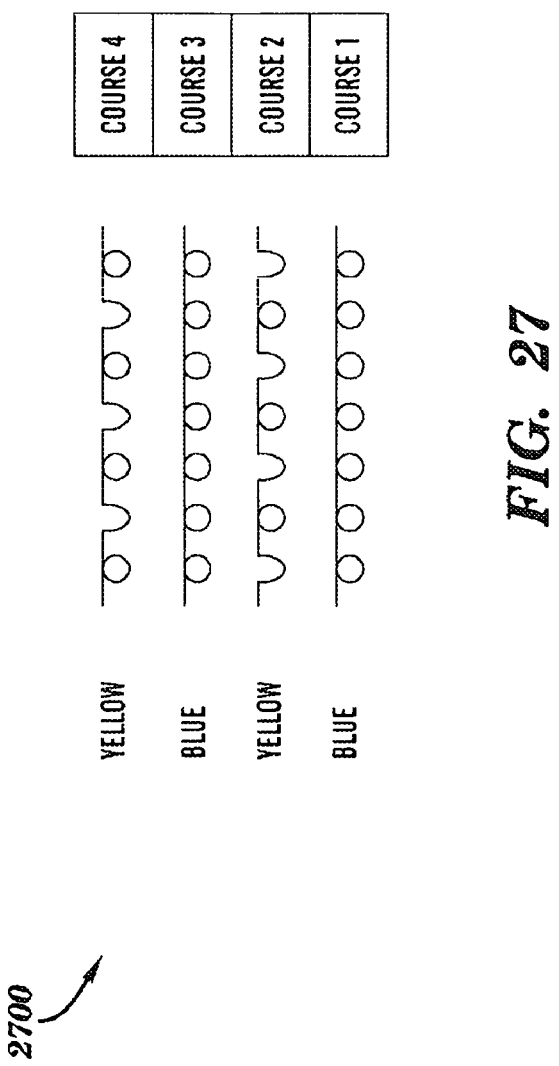
FIG. 27 illustrates an example pattern layout for the double needle bed weft knitting machine according to aspects of the present invention.

A surgical mesh device according to aspects of the present invention may be formed on the Shima Seiki flat needle bed machine as shown in the pattern layout 2700 in FIG. 27. This knit includes a continuous yarn or at least two different yarn sizes, one of which could be, though not limited to a different material. The knitted mesh would be formed by a regular jersey knit on the first row with loops formed by either a continuous yarn or a yarn of a certain yarn size, while the loops in the second row are formed by tucked loops that occur alternately with jersey knit loops of the same continuous yarn or with a yarn of a different size. The mesh would be shaped during knitting by use of increasing or decreasing stitches; a fashioning technique.

In embodiments employing silk yarn, the silk yarn may be twisted from yarn made by 20-22 denier raw silk fibers approximately 40 to 60 µm in diameter. Preferably, raw silk fibers ranging from 10 to 30 denier may be employed; however any fiber diameters that will allow the device to provide sufficient strength to the intended area are acceptable. Advantageously, a constant yarn size may maximize the uniformity of the surgical mesh mechanical properties, e.g. stiffness, elongation, etc., physical and/or biological properties. However, the yarn size may be varied in sections of the surgical mesh in order to achieve different mechanical, physical and/or biological characteristics in the preferred surgical mesh locations. Factors that may influence the size of the yarn include, but are not limited to: ultimate tensile strength (UTS); yield strength, i.e. the point at which yarn is permanently deformed; percent elongation; fatigue and dynamic laxity (creep); bioresorption rate; and transfer of cell/nutrients into and out of the mesh. The knit pattern layouts 2200, 2300, 2400, 2500, and 2600 illustrated in FIGS. 22-26, respectively, may be knitted to any width limited by the knitting machine width and could be knitted with any of the gauges available with the various crochet machine or warp knitting machine. TABLE 2 outlines the fabric widths that may be achieved using different numbers of needles on different gauge machines. It is understood that the dimensions in TABLE 1 are approximate due to the shrink factor which depends on stitch design, stitch density, and yarn size used.

TABLE 1

| Gauge | Needle Count | Knitting Width |
| --- | --- | --- |
| 48 | 2-5,656 | 0.53-2,997.68 mm |
| 24 | 2-2,826 | 1.06-2,995.56 mm |
| 20 | 2-2,358 | 1.27-2,994.66 mm |
| 18 | 2-2,123 | 1.41-2,993.43 mm |
| 16 | 2-1,882 | 1.59-2,992.38 mm |
| 14 | 2-1,653 | 1.81-2,991.93 mm |
| 12 | 2-1,411 | 2.12-2,991.32 mm |
| 10 | 2-1,177 | 2.54-2,989.58 mm |
| 5 | 2-586 | 5.08-2,976.88 mm |

Embodiments of a prosthetic device according to the present invention may be knitted on a fine gauge crochet knitting machine. A non-limiting list of crochet machines capable of manufacturing the surgical mesh according to aspects of the present invention are provided by: Changde Textile Machinery Co., Ltd.; Comez; China Textile Machinery Co., Ltd.; Huibang Machine; Jakob Muller AG; Jingwei Textile Machinery Co., Ltd.; Zhejiang Jingyi Textile Machinery Co., Ltd.; Dongguan Kyang the Delicate Machine Co., Ltd.; Karl Mayer; Sanfang Machine; Sino Techfull; Suzhou Huilong Textile Machinery Co., Ltd.; Taiwan Giu Chun Ind. Co., Ltd.; Zhangjiagang Victor Textile; Liba; Lucas; Muller Frick; and Texma.

Embodiments of a prosthetic device according to the present invention may be knitted on a fine gauge warp knitting machine. A non-limiting list of warp knitting machines capable of manufacturing the surgical mesh according to aspects of the present invention are provided by: Comez; Diba; Jingwei Textile Machinery; Liba; Lucas; Karl Mayer; Muller Frick; Runyuan Warp Knitting; Taiwan Giu Chun Ind.; Fujian Xingang Textile Machinery; and Yuejian Group.

Embodiments of a prosthetic device according to the present invention may be knitted on a fine gauge flat bed knitting machine. A non-limiting list of flat bed machines capable of manufacturing the surgical mesh according to aspects of the present invention are provided by: Around Star; Boosan; Cixing Textile Machine; Fengshen; Flying Tiger Machinery; Fujian Hongqi; G & P Görteks; Jinlong; JP; Jy Leh; Kauo Heng Co., Ltd.; Matsuya; Nan Sing Machinery Limited; Nantong Sansi Instrument; Shima Seiki; Nantong Tianyuan; and Ningbo Yuren Knitting.

Figure 1A:
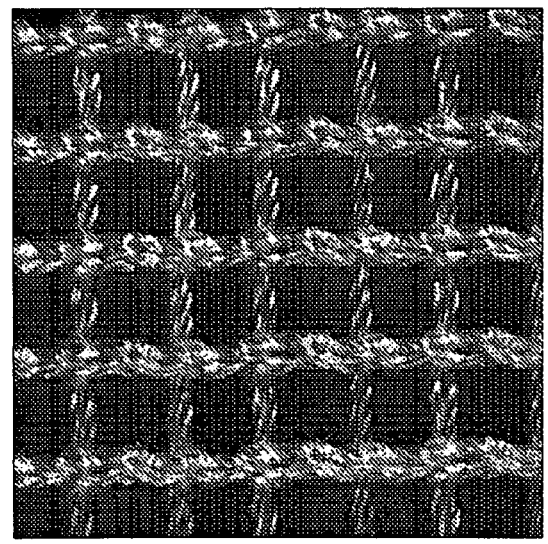
FIG. 1A illustrates the technical back of an example mesh produced on a single needle bed warp knitting machine according to aspects of the present invention.

FIGS. 1-20 illustrate example meshes produced according to aspects of the present invention. Referring to FIGS. 1A and B, an example mesh 100 is produced on a single needle bed warp knitting machine according to aspects of the present invention. FIG. 1A shows the technical back 100A of the mesh 100, and FIG. 1B shows the technical front 100B of the mesh 100.

Figure 2A:
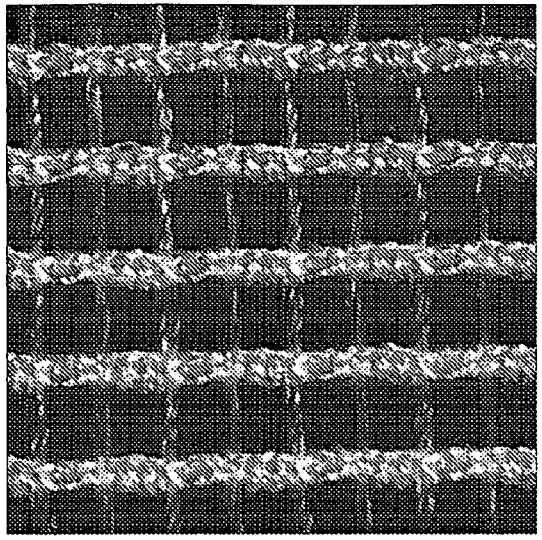
FIG. 2 illustrates an example mesh produced on a double needle bed warp knitting machine according to aspects of the present invention.
Figure 2B:
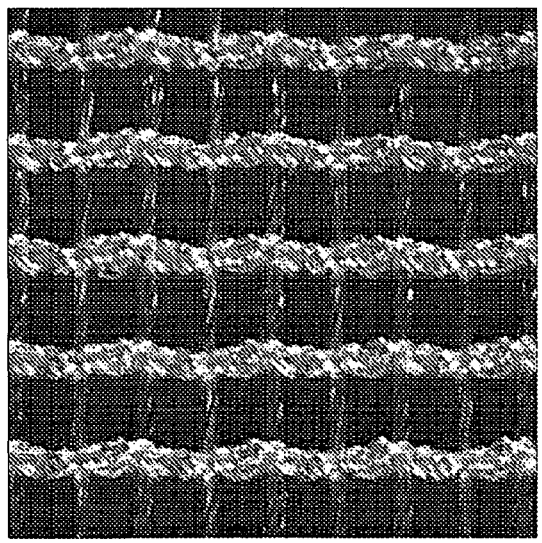

Referring to FIGS. 2A and B, an example mesh 200 is produced on a double needle bed warp knitting machine according to aspects of the present invention. FIG. 2A shows the technical front 200A of the mesh 200, and FIG. 2B shows the technical back 200B of the mesh 200.

Figure 3:
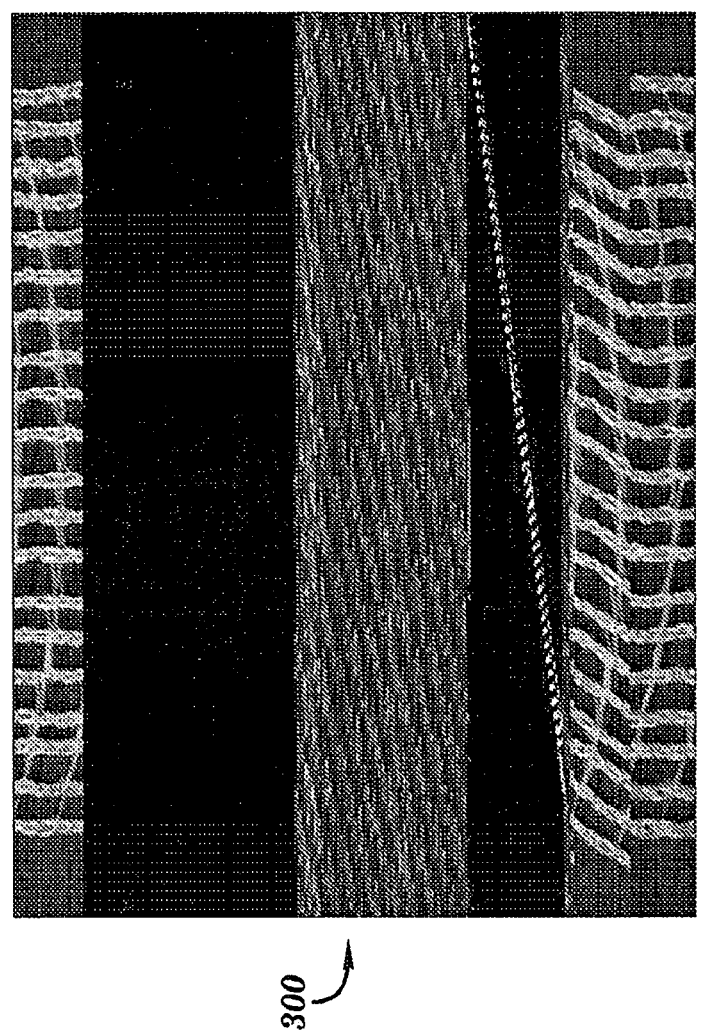
FIG. 3 illustrates an example mesh produced with single filament silk yarn according to aspects of the present invention.

FIG. 3 illustrates an example mesh 300 produced with single filament silk yarn according to aspects of the present invention.

Figure 4:
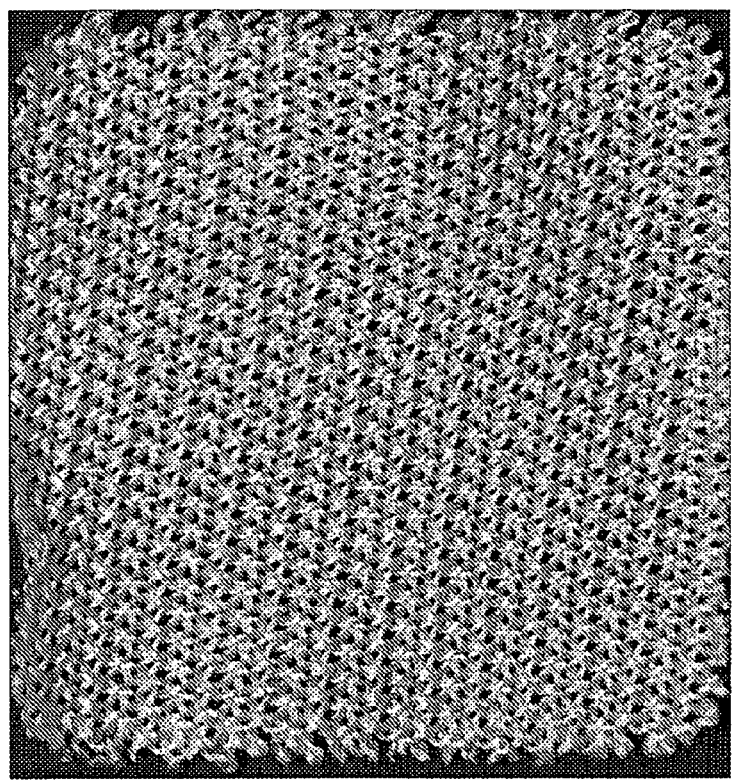
FIG. 4 illustrates an example mesh produced on a single needle bed warp knitting machine according to aspects of the present invention.

FIG. 4 shows an example mesh 400 produced on a single needle bed warp knitting machine according to aspects of the present invention.

Figure 5B:
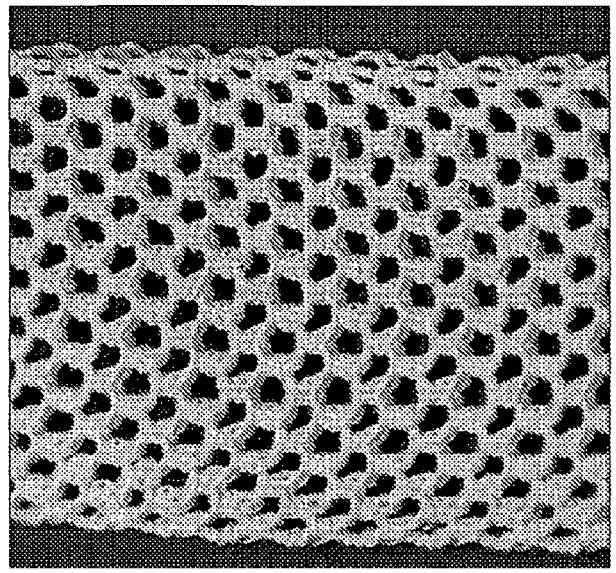
FIG. 5B illustrates an example mesh produced on a double needle bed warp knitting machine, the example mesh having a hexagonal pore according to aspects of the present invention.
Figure 5A:
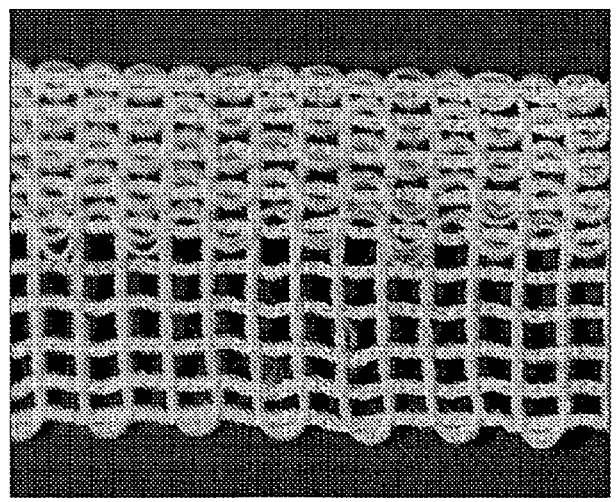
FIG. 5A illustrates an example mesh produced on a double needle bed warp knitting machine, the example mesh having a parallelepiped pore with a section demonstrating a plush design according to aspects of the present invention.

FIG. 5A illustrates an example mesh 500A produced on a double needle bed warp knitting machine. The mesh 500A has a parallelepiped pore with a section demonstrating a plush design according to aspects of the present invention. Meanwhile, FIG. 5B illustrates an example mesh 500B produced on a double needle bed warp knitting machine. The example mesh 500B has a hexagonal pore according to aspects of the present invention.

Figure 6B:
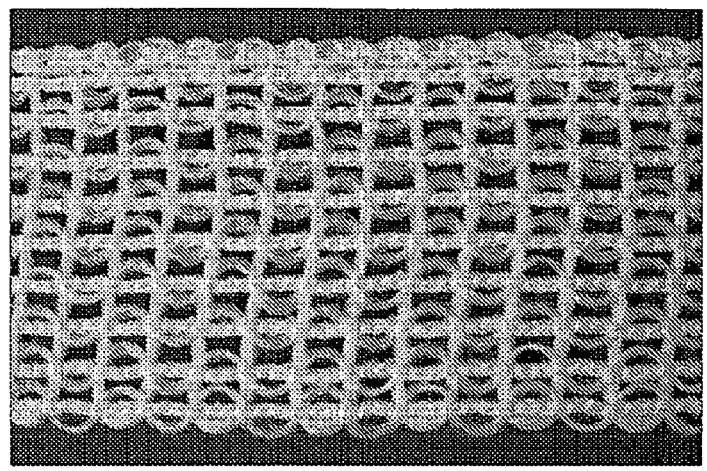
FIG. 6 illustrates example narrow mesh fabrics of varying stitch densities incorporating a plush variation according to aspects of the present invention.
Figure 6A:
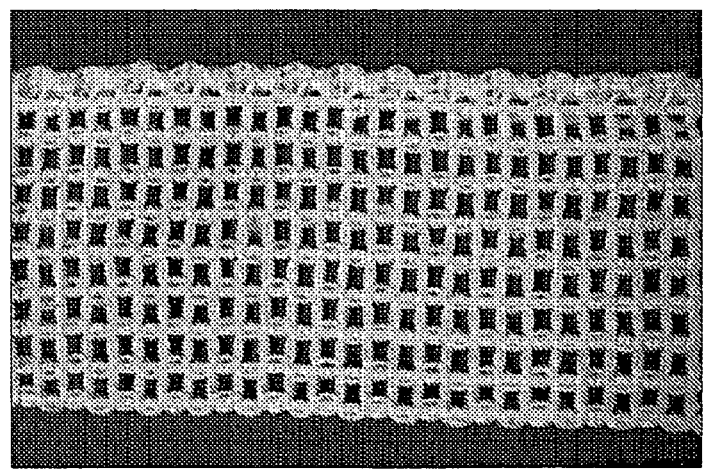

FIGS. 6A and B illustrate example narrow mesh fabrics 600A and 600B according to aspects of the present invention. The mesh fabrics 600A and 600B have varying stitch densities incorporating a plush variation.

Figure 7:
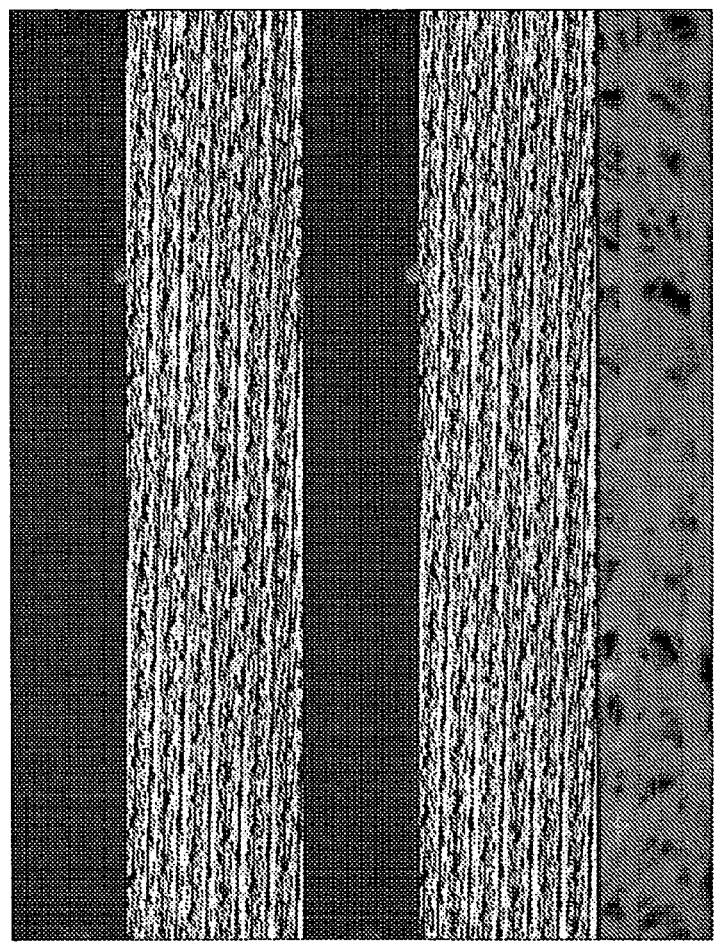
FIG. 7 illustrates an example mesh incorporating loop pile according to aspects of the present invention.
Figure 8:
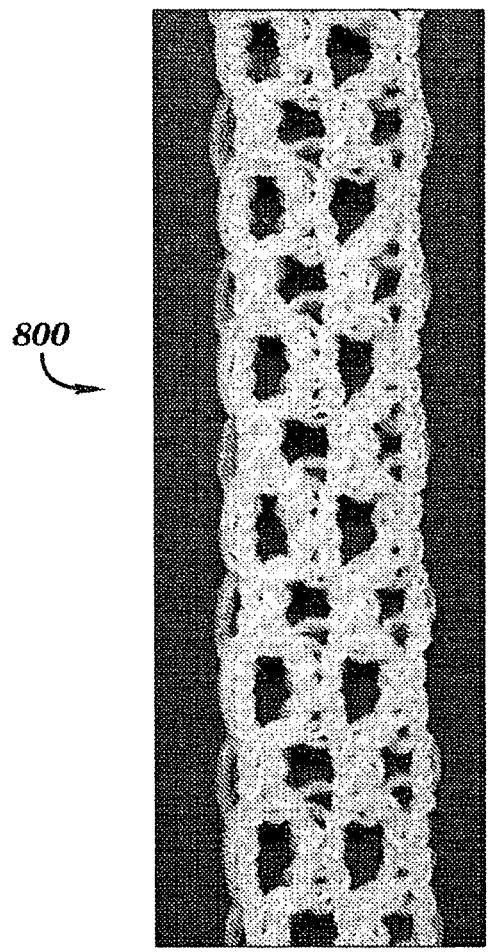
FIG. 8 illustrates an example narrow mesh fabric with pore design achieved through variation in the yarn feed rate according to aspects of the present invention.

Referring to FIG. 7, an example mesh 700 incorporates loop pile according to aspects of the present invention. FIG. 8 illustrates an example narrow mesh fabric 800 with pore design achieved through variation in the yarn feed rate according to aspects of the present invention.

Figure 9B:
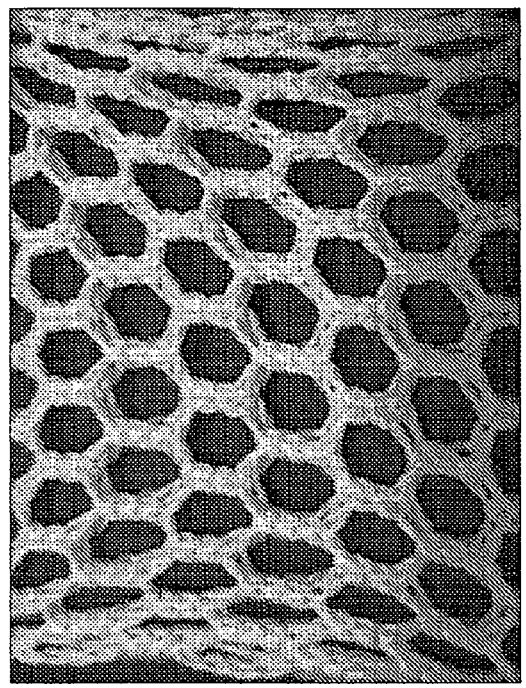
FIG. 9B illustrates an example opened mesh fabric with hexagonal shaped pores according to aspects of the present invention.
Figure 9A:
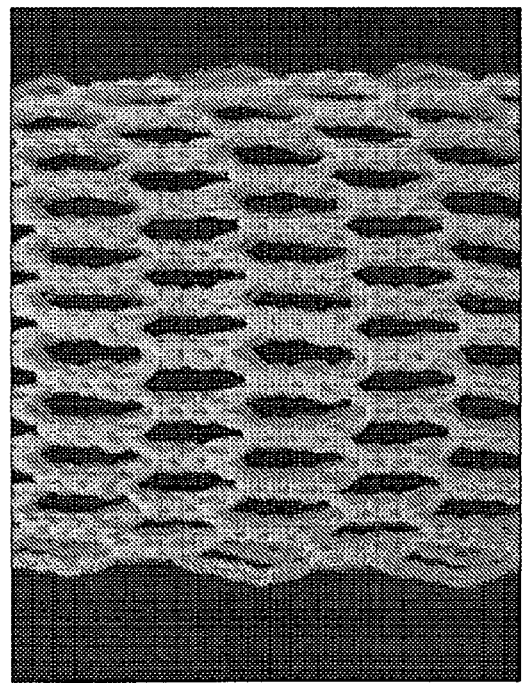
FIG. 9A illustrates an example collapsed mesh fabric with hexagonal shaped pores according to aspects of the present invention.

FIG. 9A illustrates an example collapsed mesh fabric 900A with hexagonal-shaped pores according to aspects of the present invention. Meanwhile, FIG. 9B illustrates an example opened mesh fabric 900B with hexagonal shaped pores according to aspects of the present invention.

Figure 10:
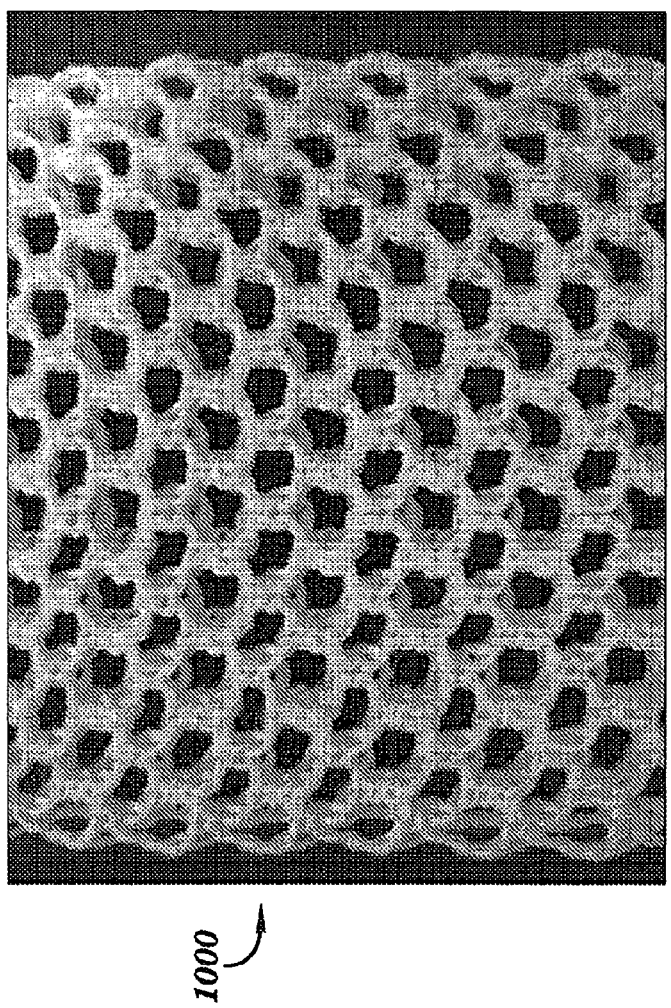
FIG. 10 illustrates an example of a stable, non-collapsible, hexagonal-shaped porous mesh fabric according to aspects of the present invention.

As shown in FIG. 10, an example of a stable, non-collapsible mesh fabric 1000 includes hexagonal-shaped pores according to aspects of the present invention.

Figure 11B:
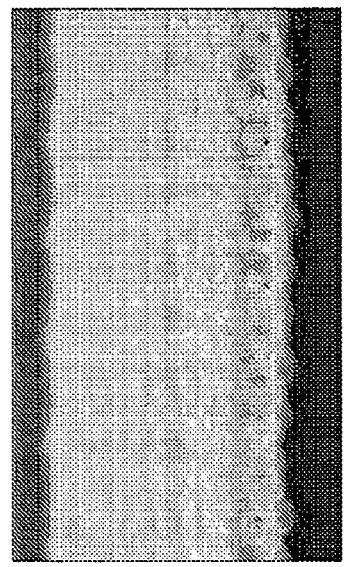
FIG. 11B illustrates the 2.55 mm thickness of the example three-dimensional mesh of FIG. 11A.
Figure 11A:
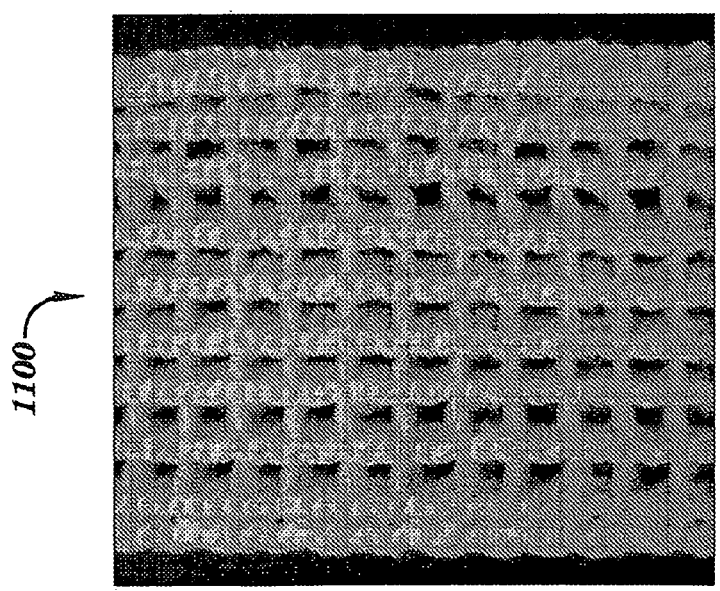
FIG. 11A illustrates an example of a three-dimensional mesh with the same technical front and technical back according to aspects of the present invention.
Figure 12:
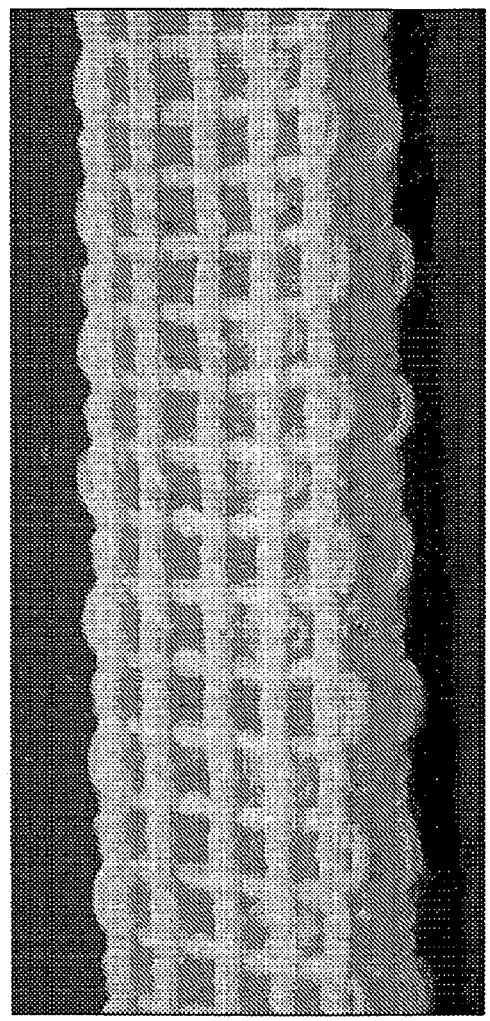
FIG. 12 illustrates an example of a three-dimensional mesh with a thickness of 3.28 mm according to aspects of the present invention.

FIG. 11A illustrate an example three-dimensional mesh 1100 with the same technical front and technical back according to aspects of the present invention. FIG. 11B illustrates the 2.55 mm thickness of the three-dimensional mesh 1100. FIG. 12 illustrates another example three-dimensional mesh 1200 with a thickness of 3.28 mm according to aspects of the present invention.

Figure 13A:
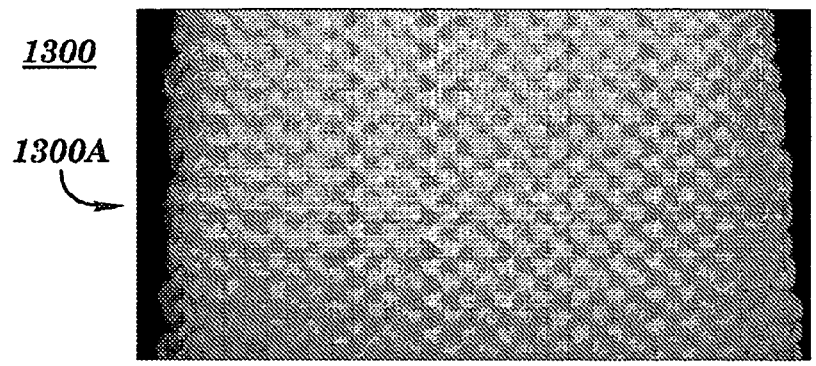
FIG. 13A illustrates the technical front of an example non-porous mesh according to aspects of the present invention.
Figure 13B:
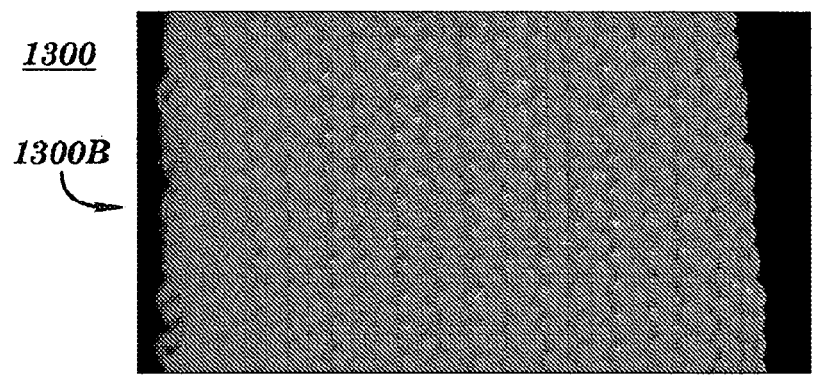
FIG. 13B illustrates the technical back of the example non-porous mesh of FIG. 13A.
Figure 13C:
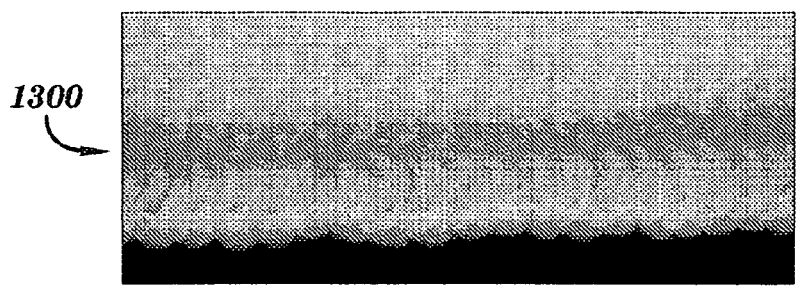
FIG. 13C illustrates the 5.87 mm thickness of the example non-porous mesh of FIG. 13A.

FIGS. 13A-C illustrate an example non-porous mesh 1300 according to aspects of the present invention. FIG. 13A shows the technical front 1300A of the non-porous mesh 1300. FIG. 13B shows the technical back 1300B of the non-porous mesh 1300. FIG. 13C shows that non-porous mesh 1300 has a thickness of 5.87 mm.

Figure 14A:
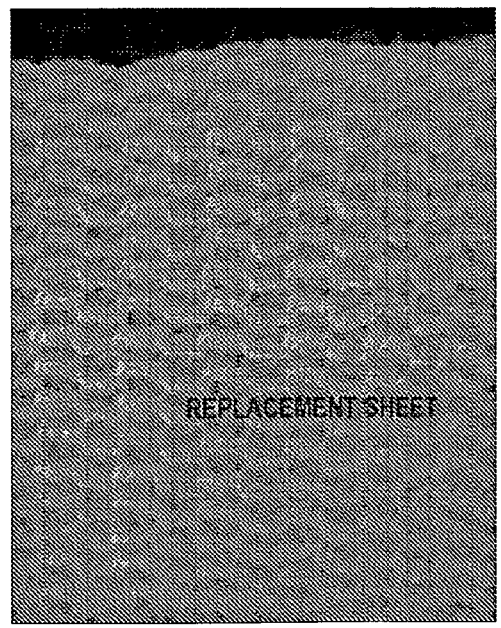
FIG. 14A illustrates an example of a three-dimensional mesh with the same technical front and technical back according to aspects of the present invention.
Figure 14B:
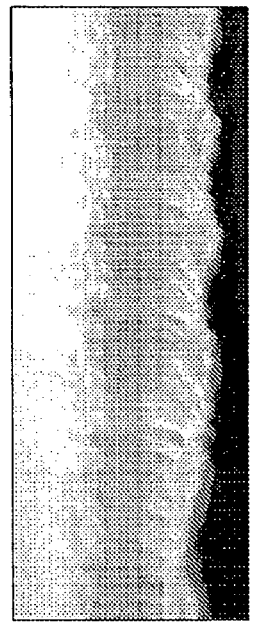
FIG. 14B illustrates the 5.36 mm thickness of the example three-dimensional mesh of FIG. 14A.
Figure 15B:
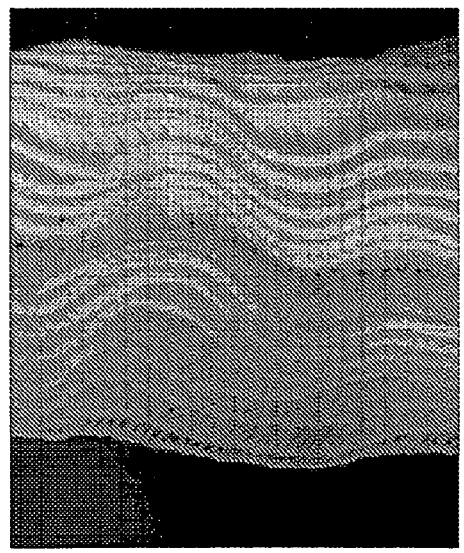
FIG. 15B illustrates the technical back of the example three-dimensional mesh fabric of FIG. 15A.
Figure 15A:
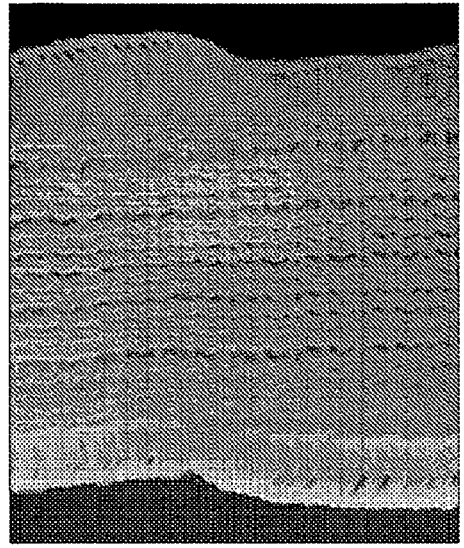
FIG. 15A illustrates the technical front of an example three-dimensional mesh fabric according to aspects of the present invention.
Figure 16:
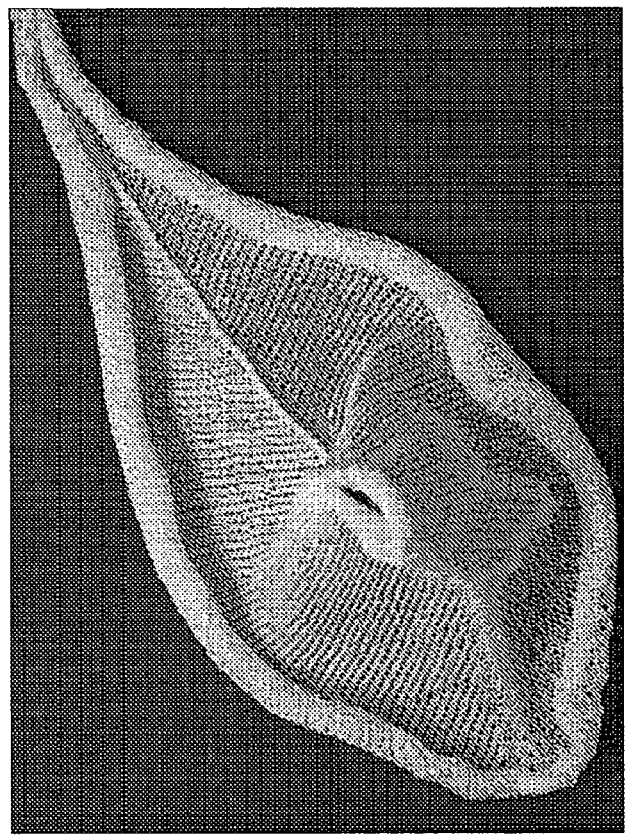
FIG. 16 illustrates an example mesh produced on a double needle bed weft knitting machine demonstrating shaping of the mesh for a breast support application according to aspects of the present invention.
Figure 17:
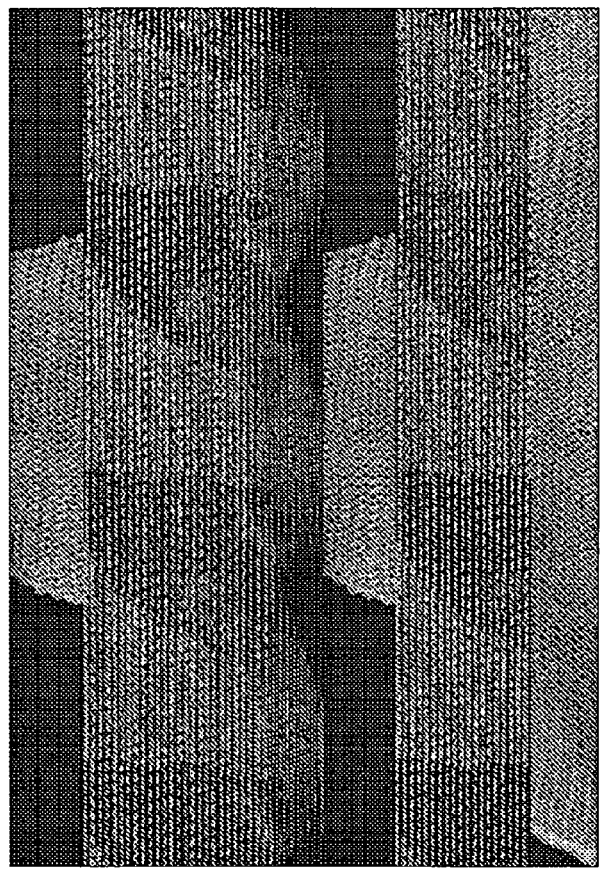
FIG. 17 illustrates another example mesh produced on a double needle bed weft knitting machine demonstrating shaping of the mesh for a breast support application according to aspects of the present invention.
Figure 18:
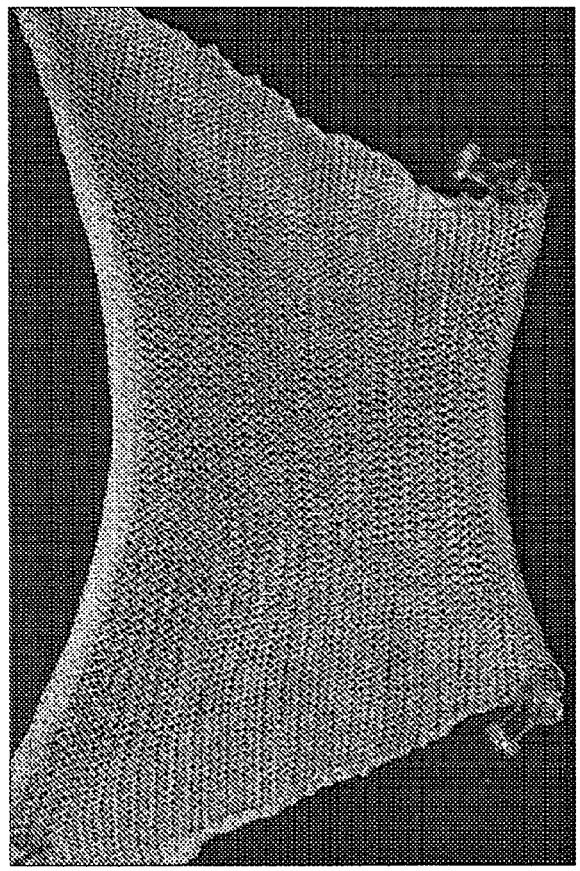
FIG. 18 illustrates yet another example mesh produced on a double needle bed weft knitting machine demonstrating shaping of the mesh for a breast support application according to aspects of the present invention.
Figure 19:
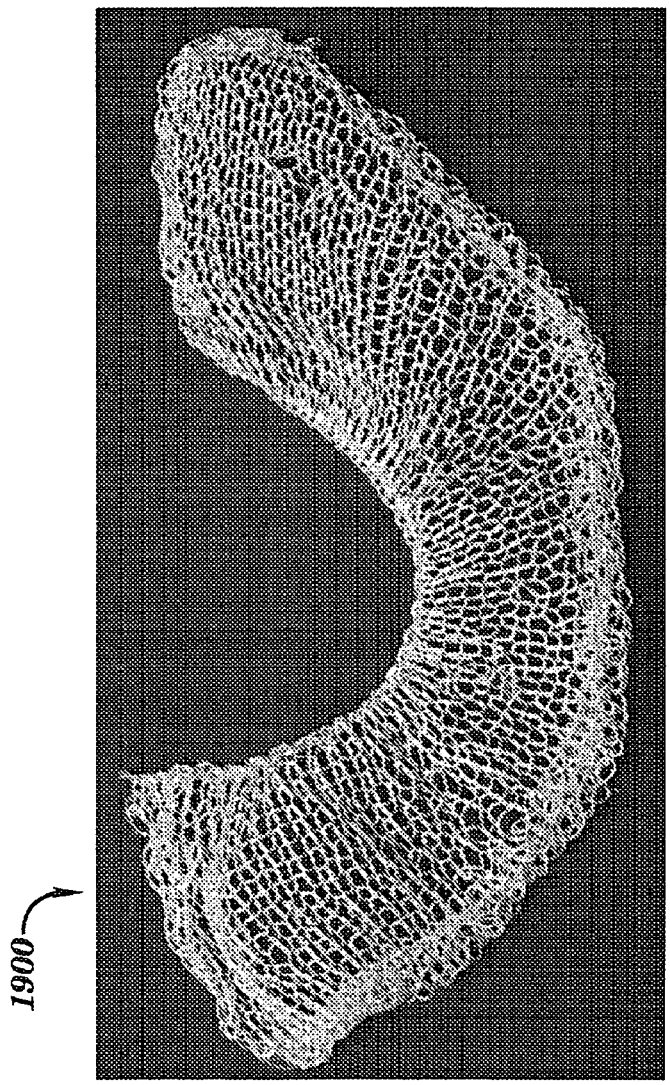
FIG. 19 illustrates a further mesh produced on a double needle bed weft knitting machine demonstrating shaping of the mesh for a breast support application according to aspects of the present invention.
Figure 20:
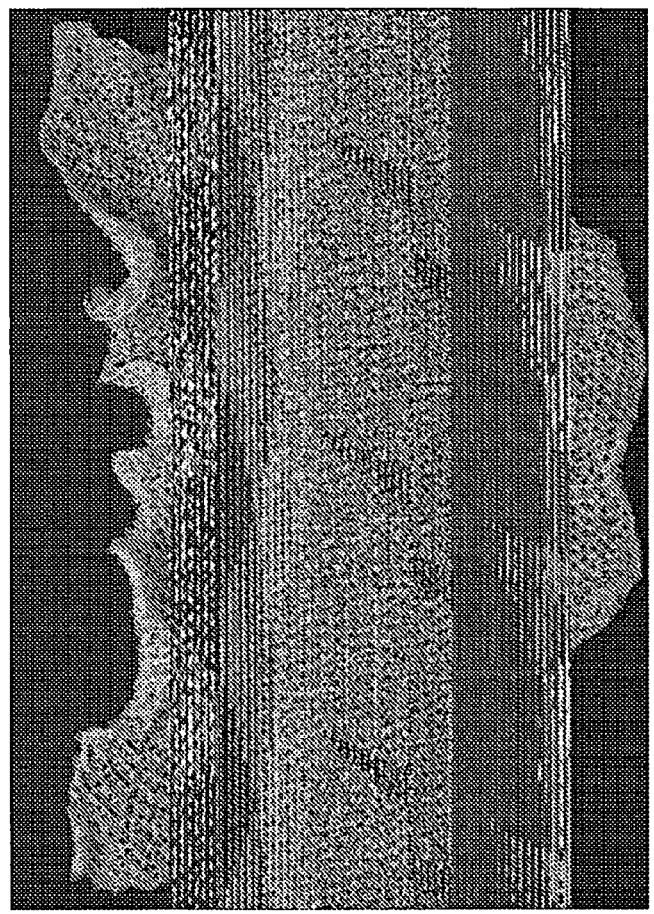
FIG. 20 illustrates another example mesh produced on a double needle bed weft knitting machine demonstrating shaping of the mesh for a breast support application according to aspects of the present invention.

FIG. 14A illustrates an example three-dimensional mesh 1400 with the same technical front and technical back according to aspects of the present invention. FIG. 14B shows that the three-dimensional mesh 1400 has a thickness of approximately 5.36 mm. FIGS. 15A and B illustrate another example three-dimensional mesh fabric 1500 according to aspects of the present invention. FIG. 15A shows the technical front 1500A of the fabric 1500, and FIG. 15B illustrates the technical back 1500B of the fabric 1500.

FIGS. 16-20 illustrate respective example meshes 1600, 1700, 1800, 1900, and 2000 that are produced on a double needle bed weft knitting machine. The meshes 1600, 1700, 1800, 1900, and 2000 demonstrate shaping of a mesh for a breast support application according to aspects of the present invention.

A test method was developed to check the cutability of the surgical mesh formed according to aspects of the present invention. In the test method, the surgical mesh evaluated according to the number of were needed to cut the mesh with surgical scissors. The mesh was found to cut excellently because it took one scissor stroke to cut through it. The mesh was also cut diagonally and in circular patterns to determine how easily the mesh unraveled and how much it unraveled once cut. The mesh did not unravel more than one mode after being cut in both directions. To determine further if the mesh would unravel, a suture, was passed through the closest pore from the cut edge, and pulled. This manipulation did not unravel the mesh. Thus, the surgical mesh is easy to cut and does not unravel after manipulation.

Embodiments may be processed with a surface treatment, which increases material hydrophilicity, biocompatibility, physical, and mechanical properties such as handling for ease of cutting and graft pull-through, as well as anti-microbial and anti-fungal coatings. Specific examples of surface treatments include, but are not limited to:

- plasma modification
- protein such as but not limited to fibronectin, denatured collagen or gelatin, collagen gels and hydrophobin by covalent link or other chemical or physical method
- peptides with hydrophilic and a hydrophobic end
- peptides contain one silk-binding sequence and one biologically active sequence—biodegradable cellulose
- surface sulfonation
- ozone gas treatment
- physically bound and chemically stabilized peptides
- DNA/RNA aptamers
- Peptide Nucleic Acids
- Avimers
- modified and unmodified polysaccharide coatings
- carbohydrate coating
- anti-microbial coatings
- anti-fungal coatings
- phosphorylcholine coatings A method to evaluate the ease of delivery through a cannula was done to make sure the surgical mesh could be used laparoscopically. Various lengths were rolled up and pushed through two different standard sized cannulas using surgical graspers. The mesh was then evaluated to determine if there was any damage done to the mesh. The mesh that was put through the cannulas was found to have slight distortion to the corner that was held by the grasper. The 16 cm and 18 cm lengths of mesh that were rolled up and pushed through the 8 mm cannula had minimal fraying and one distorted pore, respectively. It was also found that no damage was done to the cannula or septum in any of the tests. It was found that appropriately sized surgical mesh will successfully pass through a laparoscopic cannula without damage, enabling its effective use during laparoscopic procedures.

A surgical mesh device according to aspects of the present invention has been found to bio-resorb by 50% in approximately 100 days. In a study by Horan et al., Sprague-Dawley rats were used to compare the bio-resorption of embodiments according to the present invention to Mersilene™ mesh (Ethicon, Somerville, N.J.). The histology reports from the article state that after 94 days, 43% of the initial mesh of the embodiments remained compared to 96% of the Mersilene™ mesh. It was also reported that the in growth was more uniform with the mesh of embodiments than the Mersilene™ mesh. The Mersilene™ was found to have less in growth in the defect region than along the abdominal wall.

Physical properties include thickness, density and pore sizes. The thickness was measured utilizing a J100 Kafer Dial Thickness Gauge. A Mitutoyo Digimatic Caliper was used to find the length and width of the samples; used to calculate the density. The density was found by multiplying the length, width and thickness of the mesh then dividing the resulting value by the mass. The pore size was found by photographing the mesh with an Olympus SZX7 Dissection Microscope under 0.8× magnification. The measurements were taken using ImagePro 5.1 software and the values were averaged over several measurements. The physical characteristics of the sample meshes, including embodiments according to the present invention, are provided in TABLE 2.

TABLE 2

| | Physical Characterization | | |
|---|---|---|---|
| Device | Thickness (mm) | Pore Size (mm$^2$) | Density (g/cm$^3$) |
| Mersilene Mesh | 0.31 ± 0.01 | 0.506 ± 0.035 | 0.143 ± 0.003 |
| Bard Mesh | 0.72 ± 0.00 | 0.465 ± 0.029 | 0.130 ± 0.005 |
| Vicryl Knitted Mesh | 0.22 ± 0.01 | 0.064 ± 0.017 | 0.253 ± 0.014 |
| Present Embodiments - Single Needle Bed (SB) | 1.0 ± 0.04 | 0.640 ± 0.409 | 0.176 ± 0.002 |
| Present Embodiments - Double Needle Bed (DB) | 0.80 ± 0.20 | 1.27 | 0.135 ± 0.165 |

All devices were cut to the dimensions specified in TABLE 3, for each type of mechanical analysis. Samples were incubated in phosphate buffered saline (PBS) for 3±1.25 hours at 37±2° C. prior to mechanical analysis to provide characteristics in a wet environment. Samples were removed from solution and immediately tested.

TABLE 3

| Test Modality | Length (mm) | Width (mm) |
|---|---|---|
| Tensile | 60 | 10 |
| Burst | 32 | 32 |
| Suture Pull-Out | 40 | 20 |
| Tear | 60 | 40 |
| Tensile Fatigue | 60 | 40 |

Ball burst test samples were scaled down due to limitations in material dimensions. The test fixture employed was a scaled (1:2.5) version of that recommended by ASTM Standard D3787. The samples were centered within a fixture and burst with a 10 mm diameter ball traveling at a displacement rate of 60 mm/min. Maximum stress and stiffness were determined from the burst test. Results can be seen in TABLE 4.

TABLE 4

| | Burst Strength | |
|---|---|---|
| Device | Stress (MPa) | Stiffness (N/mm) |
| Mersilene Mesh | 0.27 ± 0.01 | 13.36 ± 0.85 |
| Bard Mesh | 0.98 ± 0.04 | 38.28 ± 1.49 |
| Vicryl Knitted Mesh | 0.59 ± 0.05 | 32.27 ± 1.86 |
| Pelvitex Polypropylene Mesh | 0.59 ± 0.04 | 29.78 ± 1.33 |
| Permacol Biologic Implant | 1.27 ± 0.27 | 128.38 ± 22.14 |
| Present Embodiments (SB) | 0.76 ± 0.04 | 46.10 ± 2.16 |
| Present Embodiments (DB) | 0.66 | 40.9 |

Tensile tests were performed along the fabric formation and width axes of each device. A 1 cm length of mesh on each end of the device was sandwiched between pieces of 3.0 mm thick silicone sheet and mounted in pneumatic fabric clamps with a clamping pressure of 70-85 psi. Samples were loaded through displacement controlled testing at a strain rate of 100%/s (2400 mm/min) and/or 67%/s (1600 mm/min) until failure. The ultimate tensile strength (UTS), linear stiffness and percent elongation at break can be seen in the following tables. Results can be found in TABLES 5-8. An entry of "NT" indicates that the data has not yet been tested.

TABLE 5

Tensile SPTF (Fabric Formation Axis-1600 mm/min)

| Device | Strength (N) | Stress (MPa) | Stiffness (N/mm) | % Elong. @ Break |
|---|---|---|---|---|
| Mersilene Mesh | 46.14 ± 3.15 | 10.04 ± 0.71 | 0.90 ± 0.06 | 132.1% ± 9.3% |
| Bard Mesh | 30.90 ± 2.0 | 16.64 ± 1.16 | 3.32 ± 0.26 | 106.5% ± 3.2% |
| Vicryl Knitted Mesh | 35.69 ± 3.30 | 35.89 ± 4.48 | 2.59 ± 0.33 | 89.0% ± 7.3% |
| Present Embodiments (SB) | 76.72 ± 4.36 | 10.06 ± 0.38 | 7.13 ± 0.50 | 41.5% ± 2.3% |
| Present Embodiments Mesh (DB) | NT | NT | NT | NT |

TABLE 6

Tensile SPTF (Fabric Formation Axis-2400 mm/min)

| Device | Strength (N) | Stress (MPa) | Stiffness (N/mm) | % Elong. @ Break |
|---|---|---|---|---|
| Mersilene Mesh | 43.87 ± 5.19 | 14.15 ± 1.68 | 2.18 ± 0.3 | 56.6% ± 3.5% |
| Bard Mesh | 35.29 ± 5.69 | 4.90 ± 0.79 | 0.80 ± 0.23 | 177.3% ± 13.2% |
| Vicryl Knitted Mesh | 30.88 ± 3.30 | 14.04 ± 1.50 | 0.76 ± 0.17 | 191.9% ± 14.2% |
| Pelvite Polypropylene Mesh | 23.05 ± 3.75 | 5.36 ± 0.87 | 0.57 ± 0.07 | 110.0% ± 13.6% |
| Permacol Biologic Implant | 164.52 ± 30.58 | 13.71 ± 2.55 | 23.94 ± 2.7 | 23.5% ± 3.3% |
| Present Embodiments (SB) | 72.31 ± 7.80 | 6.95 ± 0.75 | 4.31 ± 0.3 | 45.5% ± 5.2% |
| Present Embodiments (DB) | 74.62 ± 2.70 | 8.68 ± 0.31 | 4.25 ± 0.13 | 48.3% ± 2.1% |

TABLE 7

Tensile SPTF (Fabric Width Axis-2400 mm/min)

| Device | Strength (N) | Stress (MPa) | Stiffness (N/mm) | % Elong. @ Break |
|---|---|---|---|---|
| Mersilene Mesh | 31.14 ± 2.21 | 10.04 ± 0.71 | 0.90 ± 0.06 | 132.1% ± 9.3% |
| Bard Mesh | 119.80 ± 8.36 | 16.64 ± 1.16 | 3.32 ± 0.26 | 106.5% ± 3.2% |
| Vicryl Knitted Mesh | 78.96 ± 9.86 | 35.89 ± 4.48 | 2.59 ± 0.33 | 89.0% ± 7.3% |

TABLE 7-continued

Tensile SPTF (Fabric Width Axis-2400 mm/min)

| Device | Strength (N) | Stress (MPa) | Stiffness (N/mm) | % Elong. @ Break |
|---|---|---|---|---|
| Present Embodiments (SB) | 104.58 ± 3.96 | 10.06 ± 0.38 | 7.13 ± 0.50 | 41.5% ± 2.3% |
| Present Embodiments (DB) | NT | NT | NT | NT |

TABLE 8

Tensile SPTF (Fabric Width Axis-2400 mm/min)

| Device | Strength (N) | Stress (MPa) | Stiffness (N/mm) | % Elong. @ Break |
|---|---|---|---|---|
| Mersilene Mesh | 28.11 ± 2.93 | 28.11 ± 2.93 | 1.05 ± 0.13 | 128.2% ± 23.6% |
| Bard Mesh | 103.53 ± 8.92 | 14.38 ± 1.24 | 3.43 ± 0.5 | 94.0% ± 8.4% |
| Vicryl Knitted Mesh | 106.65 ± 8.46 | 48.48 ± 3.85 | 5.08 ± 0.1 | 58.6% ± 8.4% |
| Pelvite Polypropylene Mesh | 30.24 ± 5.77 | 7.03 ± 1.34 | 1.48 ± 0.1 | 89.6% ± 9.6% |
| Permacol Biologic Implant | 67.71 ± 13.36 | 5.64 ± 1.11 | 8.56 ± 2.0 | 27.4% ± 4.2% |
| Present Embodiments (SB) | 98.84 ± 4.79 | 9.50 ± 0.46 | 8.48 ± 0.3 | 39.0% ± 4.1% |
| Present Embodiments (DB) | 70.08 ± 2.55 | 8.15 ± 0.30 | 5.87 ± 0.22 | 33.6% ± 2.0% |

Tear Strength was found through a method that entailed cutting a 10 mm "tear" into the edge, perpendicular to the long axis edge and centered along the length of the mesh. The mesh was mounted in pneumatic fabric clamps as previously described in the tensile testing methods. Samples were loaded through displacement controlled testing at a strain rate of 100%/s (2400 mm/min) until failure. The load at failure and the mode of failure are shown in TABLE 9.

TABLE 9

Tear Strength

| Device | Strength (N) | Failure Mode |
|---|---|---|
| Mersilene Mesh | 110.30 ± 5.63 | Tear Failure: 6/6 |
| Bard Mesh | 181.70 ± 12.33 | Tear Failure: 6/6 |
| Vicryl Knitted Mesh | 109.35 ± 4.85 | Tear Failure: 6/6 |
| Pelvitex Polypropylene Mesh | 108.14 ± 6.95 | Tear Failure: 4/6 |
| Permacol Biologic Implant | 273.79 ± 65.57 | Tear Failure: 6/6 |
| Embodiments (SB) | 194.81 ± 9.12 | Tear Failure: 6/6 |
| Embodiments (DB) | NT | NT |

Tensile fatigue testing was preformed on the surgical mesh device according to aspects of the present invention and representative predicate types including Vicryl Mesh and Bard Mesh. Samples were loaded into the pneumatic fabric clamps as previously described in the tensile testing methods above. Samples were submerged in PBS at room temperature during cycling. Sinusoidal load controlled cycling was preformed to 60% of mesh ultimate tensile strength. Number of cycles to failure was determined during the cyclic studies and can be seen in TABLE 10, where failure was indicated by fracture or permanent deformation in excess of 200%.

TABLE 10

| Device | Tensile Fatigue Cycles, 60% UTS |
|---|---|
| Bard Mesh | 6994 ± 2987 |
| Vicryl Knitted Mesh | 91 ± 127 |
| Embodiments (DB) | 1950 ± 1409 |

A method was developed to compare the suture pull out strength of the surgical mesh device according to aspects of the present invention to other surgical mesh on the market. Tested mesh was sutured with three 3.5 mm diameter suture anchors (Arthrex, Naples, Fla.) and secured to 15 pcf solid rigid polyurethane foam. Each device was positioned with the center of the 20 mm width over the center anchor with a 3 mm suture bite distance employed during suturing of the mesh to the 3 anchors. The saw bone was mounted in the lower pneumatic fabric clamp and offset to provide loading along the axis of the device when the device was centered under the load cell. The free end of the mesh was sandwiched between the silicone pieces and placed in the upper fabric clamp with 85±5 psi clamping force. Testing was preformed under displacement control with a strain rate of 100%/s (1620 mm/min). Maximum load at break and failure mode can be seen in TABLE 11.

TABLE 11

Suture-Pull-Out

| Device | Strength/Suture [N] | Failure Mode |
|---|---|---|
| Mersilene Mesh | 13.50 ± 1.65 | Mesh Failure: 6 of 6 |
| Bard Mesh | 28.80 ± 3.39 | Mesh Failure: 6 of 6 |
| Vicryl Knitted Mesh | 12.90 ± 1.30 | Mesh Failure: 6 of 6 |
| Pelvitex Polyproplene Mesh | 18.29 ± 4.04 | Mesh Failure: 6 of 6 |
| Permacol Biologic Implant | 47.36 ± 7.94 | Mesh Failure: 6 of 6 |
| Embodiments (SB) | 41.00 ± 2.98 | Mesh Failure: 6 of 6 |
| Embodiments (DB) | 32.57 ± 2.30 | Mesh Failure: 6 of 6 |

By utilizing the pattern for the double needle bed mesh and modifying the yarn size, yarn feed rate and/or needle bed width, the surgical mesh device according to aspects of the present invention would meet the physical and mechanical properties necessary for a soft or hard tissue repair depending on the application. Such properties include pore size, thickness, ultimate tensile strength, stiffness, burst strength and suture pull out. The pore size could be modified dependent to the feed rate to create a more open fabric and the thickness could range from 0.40 mm up to as wide as 19.0 mm. With modifications to the pore size and thickness the UTS, stiffness, burst strength and suture pull out would all be modified as well, most likely tailoring the modifications of the pore size and/or thickness to meet certain mechanical needs.

This mesh, created on the flat knitting machine would be made in such a way to increase or decrease pore size and/or thickness by changing the yarn size and/or changing the loop length found within the knitting settings. The loop placements in combination with the node lock design allow changes to the shape and/or to the mechanical properties of the mesh. A biocompatible yarn with elasticity, such as highly twisted silk, could be used for shaping.

Figure 21C:
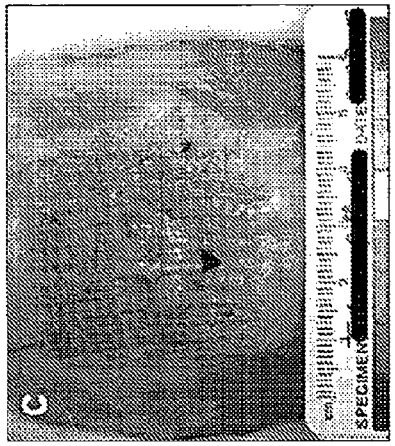
FIG. 21C illustrates an explanted specimen 94 days post implantation as shown in FIG. 21B.
Figure 21D:
FIG. 21D illustrates ball burst testing performed with a 1-cm diameter ball pushed through the defect site reinforced with the mesh according to aspects of the present invention.
Figure 21A:
FIG. 21A illustrates a full-thickness rat abdominal defect created using a custom designed 1-cm stainless steel punch, the defect appearing oval in shape due to body wall tension applied.
Figure 21B:
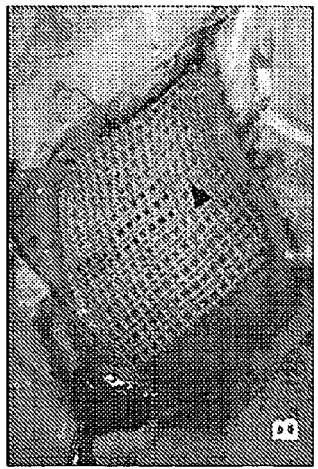
FIG. 21B illustrates a 4 cm×4 cm example implant centered on top of the open defect of FIG. 21A, and held in place with single interrupted polypropylene sutures (arrow) through the implant and muscle.

The implantation of a mesh and subsequent testing according to aspects of the present invention is illustrated in FIGS. 21A-D. FIG. 21A illustrates a full-thickness rat abdominal defect created using a custom designed 1-cm stainless steel punch. The defect appears oval in shape due to body wall tension applied. FIG. 21B illustrates a 4 cm×4 cm implant centered on top of the open defect, and held in place with single interrupted polypropylene sutures (arrow) through the implant and muscle. FIG. 21C illustrates an explanted specimen 94 days post implantation. FIG. 21D illustrates ball burst testing performed with a 1-cm diameter ball pushed through the defect site reinforced with the mesh.

While the present invention has been described in connection with a number of exemplary embodiments, and implementations, the present inventions are not so limited, but rather cover various modifications, and equivalent arrangements. For example, a knitted mesh according to aspects of the present invention may be used for a filler material. In one application, the knitted mesh may be cut into 1 mm×1 mm sections to separate one or more nodes, e.g., 3 nodes. The sections may be added to fat tissue or a hydro-gel to form a solution that can be injected into a defective area. Advantageously, the filler material may provide a desired texture, but will not unravel.

What is claimed is:

1. A method for making a biocompatible, absorbable, implantable knitted silk mesh, comprising:
   depleting sericin from yarns;
   applying a first set of the yarns in a first wale direction on a single needle bed machine, each of the first set of yarns forming a first series of loops at each of a plurality of courses for a knitted mesh;
   applying a second set of the yarns in a second wale direction on the single needle bed machine, the second wale direction being opposite from the first wale direction, each of the second set of yarns forming a second series of loops at every other of the plurality of courses for the knitted mesh; and
   applying a third set of the yarns in every predetermined number of courses for the knitted mesh, the application of the third set of yarns defining openings in the knitted mesh,
   wherein the first set of the yarns interlaces with the second set of the yarns at the every other course to define nodes for the knitted mesh, and the second set of the yarns has a greater tension than the first set of the yarns, the difference in tension substantially preventing the knitted mesh from unraveling at the nodes,
   wherein the first, second, and third sets of the yarns are formed from silk,
   thereby making the biocompatible, absorbable, implantable, knitted silk mesh.

2. The method of claim 1, wherein the first, second, and third sets of yarn are approximately 20 to 1000 μm in diameter.

3. The method of claim 1, wherein the first, second, and third sets of yarns have a substantially constant diameter.

4. A method for making a biocompatible, absorbable, implantable, knitted silk mesh, comprising:
   depleting sericin from yarns;
   applying a first set of the yarns to a first needle bed of a double needle bed machine in a wale direction;
   applying a second set of the yarns to a second needle bed of the double needle bed machine in a wale direction; and
   applying a third set of the yarns in every predetermined number of courses for the knitted mesh, the application of the third set of the yarns defining openings in the knitted mesh,
   wherein the first set of the yarns and the second set of the yarns are alternately applied to form staggered loops at the first needle bed and the second needle bed, respectively, and the first set of the yarns interlaces with the second set of the yarns to define nodes for the knitted mesh, the alternating application of the first set of the yarns and the second set of the yarns causing the first set of the yarns to have a different tension relative to the second set of the yarns at the nodes, the difference in tension substantially preventing the knitted mesh from unraveling at the nodes,
   wherein the first, second, and third sets of the yarns are formed from silk,
   thereby making the biocompatible, absorbable, implantable, knitted silk mesh.

5. The method of claim 4, wherein the first, second, and third sets of yarn are approximately 20 to 1000 μm in diameter.

6. The method of claim 4, wherein the first, second, and third sets of yarns have a substantially constant diameter.

* * * * *

UNITED STATES PATENT AND TRADEMARK OFFICE
CERTIFICATE OF CORRECTION

| | |
|---|---|
| PATENT NO. | : 8,746,014 B2 |
| APPLICATION NO. | : 13/587040 |
| DATED | : June 10, 2014 |
| INVENTOR(S) | : Enrico Mortarino |

It is certified that error appears in the above-identified patent and that said Letters Patent is hereby corrected as shown below:

On the title page, in item (57), in column 2, in "Abstract", line 10, delete "the" and insert -- The --, therefor. (1st occurrence)

On title page 3, in column 2, under "Other Publications", line 3, delete "Progess" and insert -- Progress --, therefor.

On title page 3, in column 2, under "Other Publications", line 18, delete "Nonowoven" and insert -- Nonwoven --, therefor.

In the Specification

In column 13-14, table 6, line 8, delete "Pelvite" and insert -- Pelvitex --, therefor.

In column 15-16, table 8, line 8, delete "Pelvite" and insert -- Pelvitex --, therefor.

In column 16, table 11, line 6, delete "Polyproplene" and insert -- Polypropylene --, therefor.

In the Claims

In column 17, line 27, in claim 1, delete "implantable" and insert -- implantable, --, therefor.

Signed and Sealed this
Fourteenth Day of October, 2014

Michelle K. Lee
*Deputy Director of the United States Patent and Trademark Office*